(12) United States Patent
Miller et al.

(10) Patent No.: US 6,310,058 B1
(45) Date of Patent: Oct. 30, 2001

(54) ANTIMYCOBACTERIAL AGENTS

(75) Inventors: Marvin J. Miller, South Bend; Yanping Xu, Fishers, both of IN (US)

(73) Assignee: University of Notre Dame du Lac, Norte Dame, IN (US)

( * ) Notice: Subject to any disclaimer, the term of this patent is extended or adjusted under 35 U.S.C. 154(b) by 0 days.

(21) Appl. No.: 09/578,973

(22) Filed: May 25, 2000

Related U.S. Application Data

(60) Provisional application No. 60/136,283, filed on May 27, 1999.

(51) Int. Cl.[7] .......................... A61K 31/55; C07D 413/12
(52) U.S. Cl. ........................ 514/212.08; 540/524
(58) Field of Search ........................ 540/524; 514/212.08

(56) References Cited

PUBLICATIONS

Total Synthesis of a Mycobactin . . . Maurer, P., Miller, M., J. Am. Chem. Soc., 1983, 105, 240.
Total Synthesis of a Mycobactin S: . . . Hu, J., Miller, M., J. AM. Chem. Soc., 1997, 119, 3462–3468.
Total Synthsis of Mycobactin Analogues Xu, Y Miller, M, J. Org. Chem., 1998, 63, 4314–4322.
Iron Chelators from Mycobacteria . . . Vergne, A. et al. Nat. Prod. Rep., 2000, 17, 99–116.

*Primary Examiner*—Bruck Kifle
(74) *Attorney, Agent, or Firm*—William B. Scanlon

(57) ABSTRACT

Compounds represented by the formula [1]

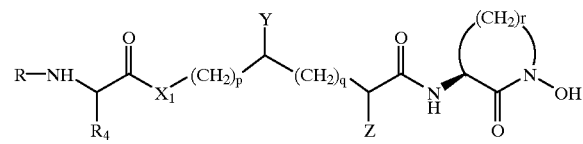

wherein R is [1a] or [1b[

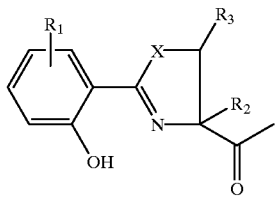

[1a]

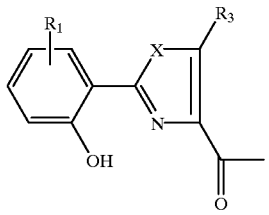

[1b]

$R_1$ is H or a substituent; $R_2$ and $R_3$ are $C_1$–$C_3$ alkyl; $R_4$ is siderophore group e.g. $CH_3$—$(CH_2)_n$—$C(O)$—$N(OH)$—$(CH_2)_m$— with n=10–22, m=2–6; X is O, S, or NH; $X_1$ is O or NH; Y is H or alkyl; Z is H or substituted amino, e.g., t-BocNH or CbzNH, and r is 2–4; are useful in the method provided for treating tuberculosis. [1] is prepared by coupling [7], wherein $HX_1$ is HO— or $H_2N$—,

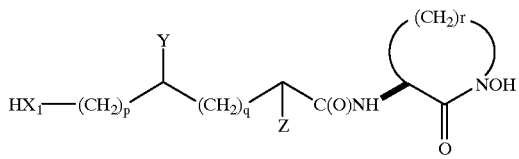

[7]

with [4] obtained as the free acid after saponification of the methyl ester.

16 Claims, No Drawings

ANTIMYCOBACTERIAL AGENTS

CROSS REFERENCE TO RELATED APPLICATION

This application is a non-provisional application claiming the benefit of Provisional application Ser. No. 60/136,283 filed May 27, 1999.

The invention described herein was carried out under National Institutes of Health Grant GM 25845.

BACKGROUND OF THE INVENTION

1. Field of Invention

This invention relates to antibiotics. In particular it relates to compounds that inhibit the causative organism of tuberculosis, *Mycobacterium tuberculosis*, to pharmaceutical formulations comprising the compounds and to a method for the treatment of tuberculosis. The compounds provided are related to the siderophoric mycobactins which are key in the transport of iron into mycobacterium and the growth thereof.

2. Description of Related Art

The family of mycobactin compounds was first isolated by Snow; Snow, G. A. *Bacteriol. Rev.* 1970, 34, 99. Structural work with the mycobactin factors was reported by Hu, Jingdan, Miller, Marvin J. *J. Am. Chem. Soc.* 1997, 119, 3462–3468 and Xu, Yanping, Miller, Marvin J. *J. Org. Chem.* 1998, 63, 4314–4322.

The latter publication describes analogs of mycobactins obtained via retrograde synthesis and the antimycobacterium activity obtained with the analogs.

SUMMARY OF THE INVENTION

The compounds provided by this invention are represented by the structural formula 1.

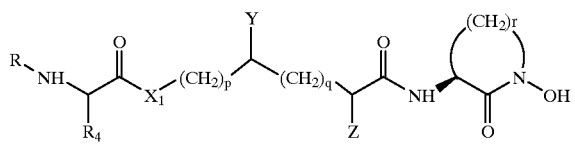

Formula [1]

wherein R is a 2-phenyl oxazoline, thiazoline or imidazoline group represented by the formula (1a)

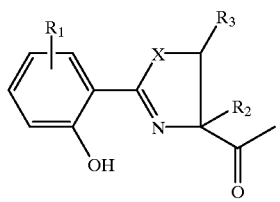

(1a)

or a 2-phenyl oxazole, thiazole or imidazole group represented by the formula (1b)

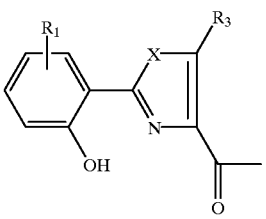

(1b)

$R_1$ is hydrogen or a substituent group e.g. lower alkyl, lower alkoxy, hydroxy, carboxy, amino or mono- or dialkylamino, aminocarbonyl, mono- or dialkylaminocarbonyl; or —$C_1$–$C_4$ alkyl substituted by one or two phenyl groups; $R_2$ and $R_3$ independently are hydrogen or $C_1$–$C_3$ alkyl; $R_4$ is a siderophoric group represented by the formula —$(CH_2)_m$—N(OH)—C(O)—$(CH_2)_n$—$(CH=CH)_o$—$CH_3$;

X is O, S, or NH;

$X_1$ is O or NH;

Y is H or $C_1$–$C_4$ alkyl;

Z is H, lower alkyl, mono or dialkylamino or $N(R_5)(R_5')$ when $X_1$ is NH and when $X_1$ is O, Z is mono or dialkyamino or $N(R_5)(R_5')$ wherein $R_5$ is hydrogen, lower alkyl, alkyloxycarbonyl, aryloxycarbonyl; aralkyloxycarbonyl, cycloalkoxycarbonyl, bicyloalkoxycarbonyl or lower alkanoyl; $R_5'$ is hydrogen or lower alkyl;

m is an integer of from 2 to 6;

n is an integer of from 0 to 22;

o is an integer of from 0 to 4 provided that m+0 is no greater than 25;

p and q independently are 0, 1 or 2;

r is an integer of from 2 to 4;

and the pharmaceutically acceptable salts thereof.

The compounds of the invention are useful antimycobacterial agents useful in the treatment of tuberculosis according to the method provided herein. Pharmaceutical formulations also are provided.

DETAILED DESCRIPTION

The terms used in the formula 1 have the following meanings herein. Lower alkyl refers to straight or branched chain hydrocarbon radicals having from 1 to 6 carbon atoms such as e.g., methyl, ethyl, n-propyl, iso-propyl, n-butyl, sec-butyl, t-butyl, n-amyl, iso-amyl, n-hexyl, and the like. Lower alkoxy refers to methoxy, ethoxy, n-propoxy, iso-propoxy, n-butoxy, t-butoxy, and the like. Halogen refers to fluoro, chloro, and bromo. Mono- and dialkylamino refers to the amino group substituted by one or two of the same or different alkyl groups having from 1 to 4 carbon atoms such as e.g., methylamino, dimethylamino, ethylamino, methylethylamino, diethylamino, n-propylamino, iso-propylamino, t-butylamino, methyl-t-butylamino and the like. Mono- and dialkylaminocarbonyl refers to the aminocarbonyl group wherein the amino group is substituted as defined above for mono- and dialkylamino groups. $C_1$–$C_4$ alkyl substituted by one or two phenyl groups refers to benzyl, diphenylmethyl, 2-phenylethyl, 1,2-diphenylethyl, 4-phenylbutyl, 1,3-diphenylpropyl and the like.

The groups represented in the formula [1] wherein Z is $N(R_5R_5')$ include for example where $R_5'$ is a $C_1$–$C_6$ alkoxycarbonyl group such as e.g., methoxycarbonyl, ethoxycarbonyl, iso-propoxycarbonyl, secbutyloxycarbonyl, t-butyloxycarbonyl (t-Boc), iso-amyloxycarbonyl, and straight and branched hexyloxycarbonyl groups; the cycloalkoxycarbonyl groups having from 3 to 7 ring carbon atoms such as e.g., cyclopropyloxycarbonyl, cyclobutyloxycarbonyl, cyclopentyloxycarbonyl, cyclohexyloxycarbonyl and cycloheptyloxycarbonyl; the aryloxycarbonyl groups wherein aryl is phenyl or naphthyl such as e.g., phenyloxycarbonyl, 2,6-dimethylphenyloxycarbonyl and 1- or 2-naphthyloxycarbonyl; the aralkyloxycarbonyl groups such as e.g., benzyloxycarbonyl, 2,6-dimethylbenzyloxycarbonyl, 2-phenyl-2-propyloxycarbonyl, and 2,6-dichlorobenzyloxycarbonyl; bicycloalkoxycarbonyl groups such as e.g., bicycloheptyloxycarbonyl, adamantyloxycarbonyl, bicyclohexyloxycarbonyl, and the like. The mono or dialkylamino groups represented by Z include, for example, sec-butylamino, t-butylamino, diethylamino, iso-propylamino, di-n-propylamino, pentylamino, hexylamino, dihexylamino, and like mono or di-($C_1$–$C_6$ alkyl) amino groups.

In the formula (1) where, in $R_4$ o is greater than 1, the ethylene groups can be conjugated or non-conjugated. For example, m+o can represent $(CH_2)_2CH=CHCH=CH(CH_2)_9CH_3$, $(CH_2)_2CH=CH(CH_2)_2CH=CH(CH_2)_9CH_3$ and the like. When o is greater than 0, the double bonds can be epoxidized or converted to diols by standard procedures.

The cyclic-hydroxyamino groups represented when r of —$(CH_2)_r$— is 2 to 4 are N-hydroxypyrrolidin-2-one, N-hydroxypiperidin-2-one and N-hydroxyazepin-2-one.

The compounds represented by the formula 1 are obtained by the methods described by Xu, Yanping, and Miller, Marvin J. *J. Org. Chem.* 1998, 63, 4314–4322, employing a retrograde synthesis approach. The process for preparing the compounds of the invention is a multi-step process. Solely for purposes of ease of description herein, the compounds of the formula 1 are referred to in two portions. The portion shown to the left of formula 1 as drawn above and represented by the partial formula R—NH—CH($R_4$)—C(O)— is referred to as the "mycobactic acid" portion. For example, as represented by the formula [4] below as the free acid or as an ester thereof. The portion to the right in formula 1 beginning with $X_1$ as shown is referred to as the "cobactin" portion. For example as represented by the formula [7] below. The coupling of the mycobactic acid portion with the cobactin portion provides the compound of the invention.

Initially the compound represented by the formula 2

[2]

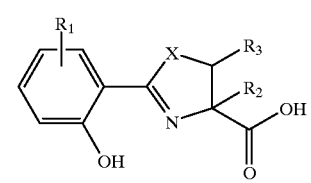

is coupled with an ω-(N-acyl-N-protected or unprotected hydroxyamino) amino acid ester [3] represented by the formula $CH_3$—$(CH_2)_n$—C(O)—N—(OH)—$(CH_2)_m$—CH—($NH_2$)$COOCH_3$ wherein the N-hydroxy group may be protected with a silyl protecting group, preferably [2-(trimethylsilyl)ethoxy] methyl group. The coupling reaction is carried out in an inert solvent with a diimide e.g. 1-ethyl-3-[3-(dimethylamino)propyl] carbodiimide in the presence of 1-hydroxy-7-azabenzotriazole and 4-(dimethylamino) pyridine providing the coupling product referred to herein as an ester of a mycobactin acid and represented by the following formula [4], wherein X is O, having the siderophore hydroxyamino acyl group.

[4]

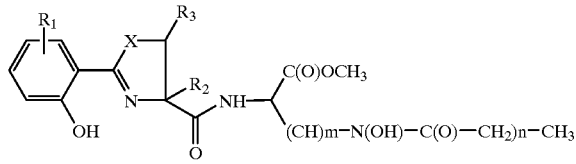

A like coupling product is obtained under the same conditions with the heterocyclic acid represented by the formula [5], e.g. an oxazole-2-carboxylic acid.

[5]

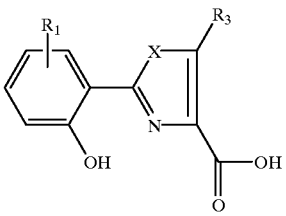

The ω-(N-acyl-N-protected hydroxyamino)-α-protected-amino acid [3], is obtained by the oxidation of the ω-amino-α-protected amino acid with dimethyldioxirane (DMD) (Hu, J.; Miller, M. J. *J.Org. Chem.* 1994, 59, 4858). After oxidation, the N-hydroxyamino group is acylated on the amino group with the acid $CH_3$—$(CH_2)_n$—COOH. The acylation is carried out with an acyl halide or active ester of the acid. For example, stearyl chloride is reacted in an inert solvent with the amine in the presence of a base such as sodium bicarbonate. Acids which are used include capric acid, lauric acid, myristic acid, palmitic acid, hebenic acid, and like fatty acids. The N—(OH) group is protected prior to use in the coupling reaction. Useful in protecting the hydroxy group are the silyl protecting groups such as trimethylsilyl, t-butyldimethylsilyl, or [2-(trimethylsilyl)ethoxy]methyl.

The 2-phenylheterocylic compound [2] or [5] is obtained with a substituted or unsubstituted salicylic acid by coupling the acid with an α-amino acid ester represented by the formula

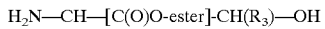

$H_2N$—CH—[C(O)O-ester]-CH($R_3$)—OH wherein $R_3$ has the same meanings as defined for formula [1]. The amide formed is cyclized with Burgess' reagent (Wipf, P.; Miller, C. P. *J. Org. Chem.* 1983, 58, 1575) to form the oxazoline (X=O) or with Lawesson's reagent [2,4-bis (p-methoxyphenyl)-1,3-dithiadiphosphetane-2,4-disulfide] to form the thiazoline (X=S). The preparation of compound [2] is illustrated in the following reaction Scheme 1 wherein X is O.

Reaction Scheme 1

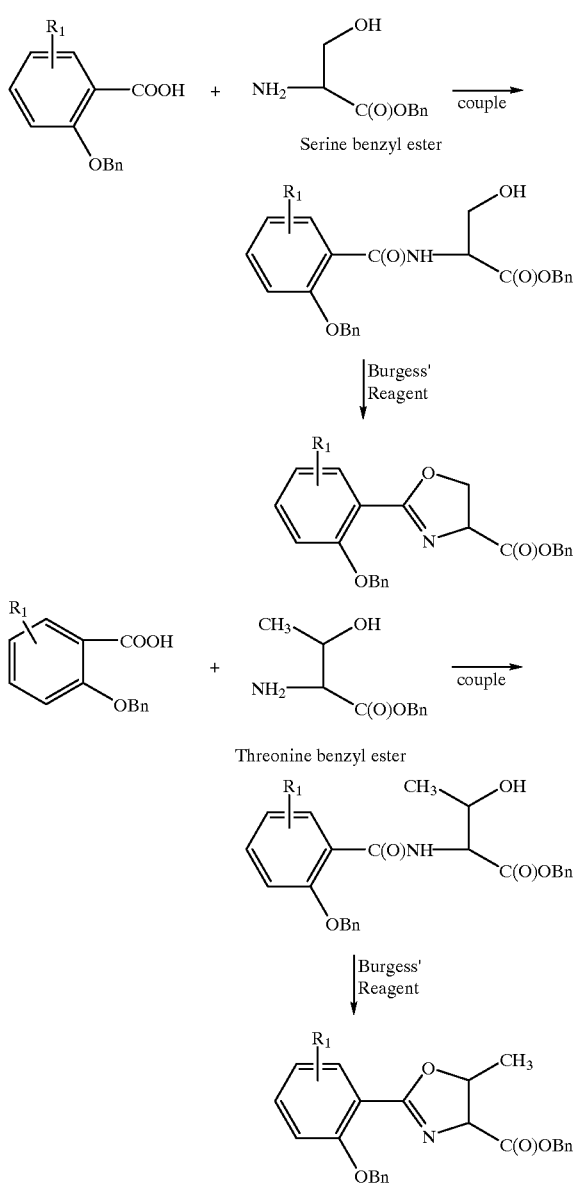

The corresponding thiazoline compound wherein X is S is prepared in the same manner except that the amide obtained is cyclized with Lawesson's reagent.

Compound [2] wherein X is NH is prepared by the reaction of a 3-protected amino-2-aminopropionic acid ester with the substituted salicylic acid to form the amide. The amino protecting group of the amide is removed after coupling and lastly, the free amino amide is treated under dehydrative conditions to form the imidazoline compound.

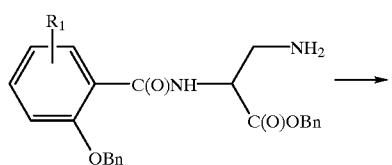

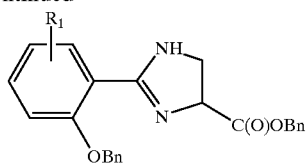

The 3-protected amino-2-aminopropionic acid ester used in the preparation of the imidazoline compounds is prepared via the β-lactam [15] as described herein below for the preparation of [9]. The protected 3-amino group of the 2,3-diaminopropionic acid ester derivative [16] is deprotected to provide the free amine used in the coupling reaction to provide the amide which is then cyclized.

The compounds represented by the formula [2] wherein $R_2$ is $C_1$–$C_3$ alkyl are obtained with an ester of a compound of formula [2] wherein $R_2$ is hydrogen by alkylation with an alkyl iodide and a base. Preferably the base is sodium dimethylsilylamide or like base. The preparation is illustrated below.

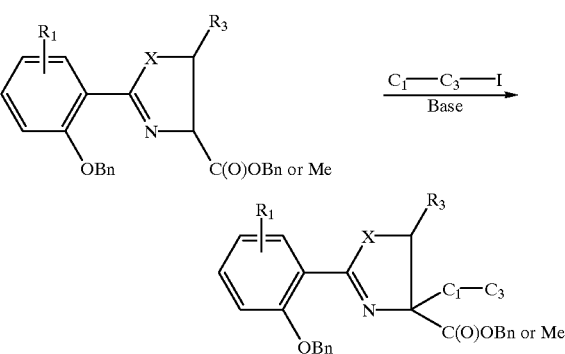

The oxazole, thiazole and imidazole compounds represented by the formula [5] are obtained by reacting the oxazoline, thiazoline or imidazoline with dichlorodicyanoquinone (DDQ) as shown below.

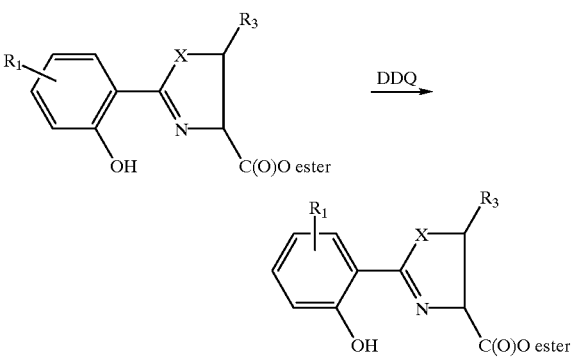

Next in the synthesis of compound [1], an amino ester or hydroxy ester represented by the formula

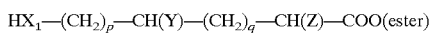

wherein X1 is NH or O, and p, q, Y and Z have the same meanings as defined for formula [1], is deesterified by saponification and the free acid is coupled with a 3-amino-N-hydroxypyrrolidone-2, a 3-amino-N- hydroxypiperidone-2 or a 3-amino-N-hydroxyazepine-2-one represented by the formula [6].

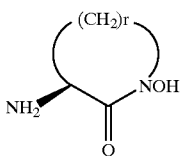

[6]

wherein r is as defined for formula [1]. The formula [6] compound of the cobactin portion is prepared as described by Hu, J., and Miller, M. J. *J. Am. Chem. Soc.* 1997, 119, 3462–3468. When $HX_1$ or Z is an amino group the group is protected or blocked from interfering in the desired coupling reaction. Commonly used amino protecting groups such as, e.g. an alkoxy carbonyl group such as t-Boc or an aryloxycarbonyl group such as benzyloxycarbonyl can be used. The hydroxy group of the hydroxyamnino group in the ring can be protected during the coupling reaction. However, under the coupling conditions described below, the N-hydroxy group need not be protected. While a number of hydroxy protecting groups are useful the tert-butyldimethylsilyl or the tert-butyldiphenylsilyl groups are preferred. Following the reaction the protecting groups are optionally removed to obtain the product represented by the following structural formula [7].

Formula [7]

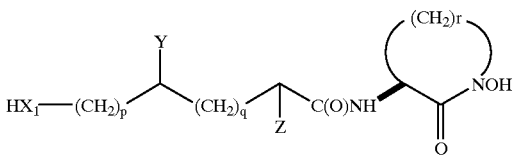

The coupling reaction is carried out in DMF or other suitable inert solvent with a water soluble carbodiimide e.g., 1-ethyl-3-[3-(dimethylamino)propyl] carbodiimide hydrochloride and the active ester reagent 1-hydroxy-7-azabenzotriazine. The coupling product [7] is referred to herein for convenience as the cobactin portion of the formula [1] compound.

To complete the synthesis of the formula [1] compound the ester [4] is deesterifed and the free acid form of the mycobactin portion obtained is used to acylate the compound [7] the cobactin portion of formula [1] where, in [7], $HX_1$ is amino or hydroxy. Any free amino group of Z or $R_1$ is protected during the coupling. When $HX_1$ is hydroxy the ester of [4] and [7] is obtained while when $HX_1$ is an amino group the corresponding amide is obtained.

The compounds of the invention inhibit the growth of *Mycobacterium tuberculosis*. In in vitro tests carried out at the Tuberculosis Antimicrobial Acquisition and Coordinating Facility of the Southern Research Institute vs. *M. tuberculosis* H37Rv the compounds listed below showed the designated % inhibition at the concentration indicated. The compound [37 Y=H] herein represented by the formula 1 wherein R=(1a), X=O, $R_1=R_2=R_3=H$, $X_1=O$, m=4, n=15, Y=H, Z=NHCbz, p=q=0, and r=4; 44% inhibition at 12.5 μg/mL. The compound [37 Y=Me] herein having the same structure as the preceding compound; 48% inhibition at the same concentration. The compound [40a] having the same structure as the first above except that $X_1$ is NH and Z=H; 25% inhibition at the same concentration. The compound [8] herein having the same structure as the first above except that $X_1$ is NH and Z is NH-t-Boc; 98% inhibition at a concentration of 0.2 μg/mL. In the foregoing Cbz=benzyloxycarbonyl and t-Boc=tert-butyloxycarbonyl.

Preferred compounds of the invention are represented when $X_1$ is O or NH and Z is $N(R_5)(R_5')$ wherein $R_5$ is H and $R_5'$ is an arylalkoxycarbonyl, alkyloxycarbonyl, cycloalkoxycarbonyl or bicycloalkoxycarbonyl group. Further preferred compounds are represented wherein R is the heterocycle (1a), X is O, $X_1$ is O or NH and Z has the same meanings as in the above preferred group.

A preferred compound of the invention is represented by the formula [8] below.

[8]

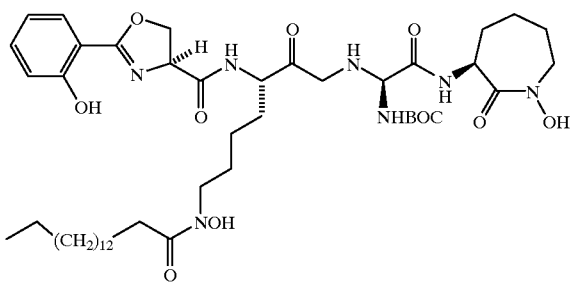

As shown in the above formula for compound [8], the term Z of [7] represents the S isomer wherein the NHBOC group is above the plane. The R isomer, wherein the NHBOC group is below the plane has been prepared by using the corresponding isomer of t-BOC protected serine in the preparation of the cobactin portion of the compound.

The preparation of the preferred compound [8] is carried out as depicted in Reaction Scheme 2 below. As shown, cobactin portion [9] is debenzylated with hydrogen over 10% palladium on carbon catalyst to provide the free amine [10]. The free amine is coupled with the mycobactin acid portion [11] with the carbodiimide ethyldimethylaminopropylcarbodiimide (EDC HCl) in DMF and 1-hydroxy-7-azabenzotriazine (HOAt) to provide compound [12] wherein the N-hydroxy group of the cobactin portion is protected with a silyl group. Removal of the silyl group (the t-butyldiphenylsilyl group, TBDPS) by treatment with tetrabutylammonium fluoride (TBAF) provides the preferred compound [8].

Reaction Scheme 2

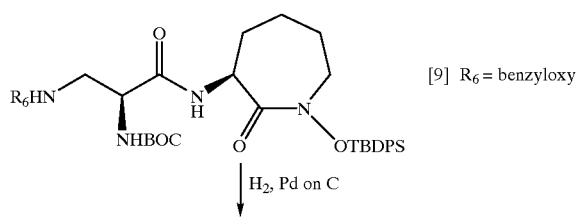

[9] $R_6$ = benzyloxy

H$_2$, Pd on C

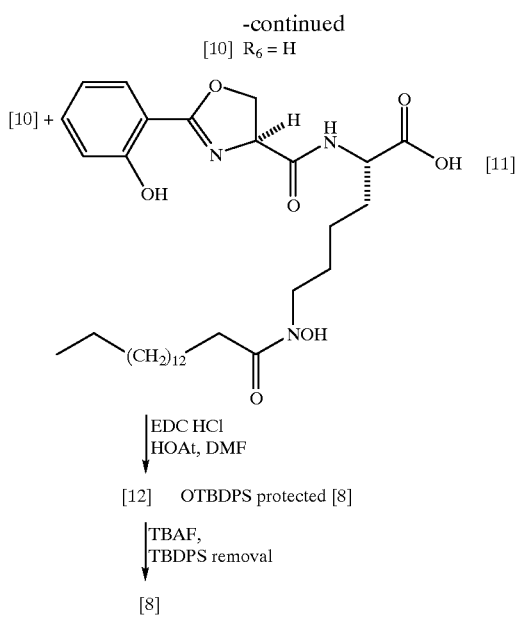

[10] R₆ = H

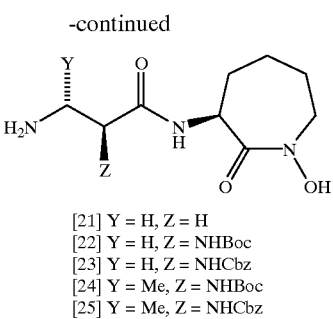

[21] Y = H, Z = H
[22] Y = H, Z = NHBoc
[23] Y = H, Z = NHCbz
[24] Y = Me, Z = NHBoc
[25] Y = Me, Z = NHCbz

A specific embodiment of the invention illustrating the preparation of a compound of the formula [1] is shown below in Reaction Scheme 3. The protected amino group of the cyclic compound [26] is removed to provide the free amine [27]. The free amine is coupled with the amino acid to provide the amide [28]. The ω-(hydroxyamino) amino acid ester [30] with the hydroxy group of the hydroxyamino group either protected or unprotected is acylated with the fatty acid chloride to provide [31] or [32]. Either compound is reduced catalytically to provide the free amino acid ester [33a] or 33b]. As shown, [33b] is coupled with the 2-(2-hydroxyphenyl)oxazoline-4-carboxylic acid to yield the mycobactic acid ester [34]. The ester [34] is saponified and the free acid [35] is coupled with the cobactin [28] or [29] to yield [36] or [36a].

The cobactin portion [9] is prepared as follows. t-Boc protected L-serine [13] is coupled with O-benzylhydroxylamine at pH 4–5 with EDC.HCl to provide the hydroxamate [14]. The hydroxamate is cyclized in acetonitrile with triphenylphosphine-carbon tetrachloride in the presence of triethylamine to form the β-lactam [15]. The β-lactam is saponified with lithium hydroxide in THF-water to provide, in 100% yield, cleavage of the ring to form 2,3-diaminopropionic acid derivative [16]. Lastly, the derivative [16] is coupled with the seven-membered azepine-2-one [6], wherein r is 4, to provide the N-benzyloxy derivative of the cobactin portion [9]. The foregoing preparation of [9] is shown schematically below. Hu, J.; Miller, M. J. *J. Am. Chem. Soc.* 1997, 119, 3462.

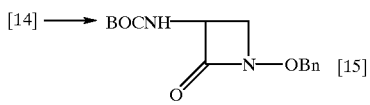

[15] $\xrightarrow{\text{LiOH}}$ BnONHCH₂CH(NHBOC)COOH  [16]

[16] + [6] r = 4 $\xrightarrow{\text{Couple}}$ [9] R₆ = benzyloxy

Examples of cobactin portions represented by the formula [7] wherein p and q are 0 are shown below.

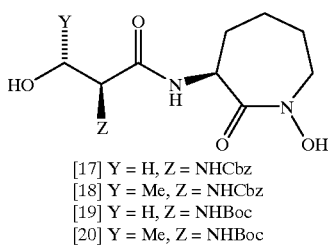

[17] Y = H, Z = NHCbz
[18] Y = Me, Z = NHCbz
[19] Y = H, Z = NHBoc
[20] Y = Me, Z = NHBoc

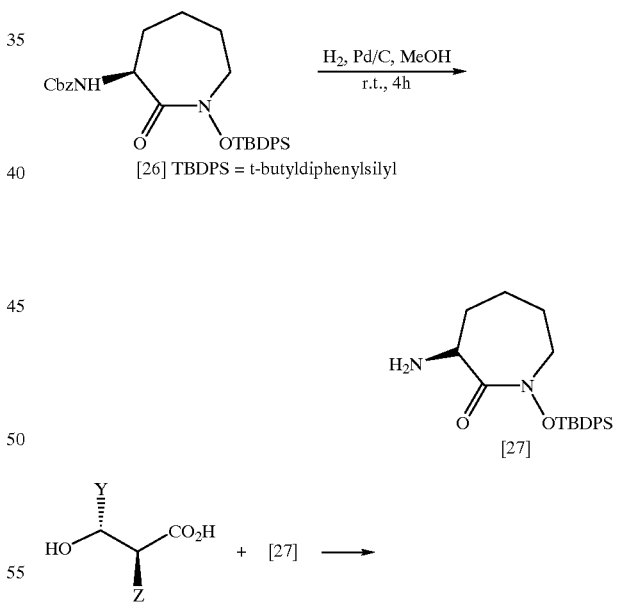

[26] TBDPS = t-butyldiphenylsilyl

Y = H or Me

[28] Y = H; [29] Y = Me

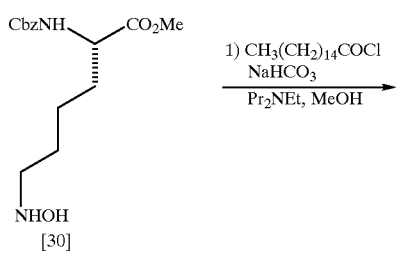
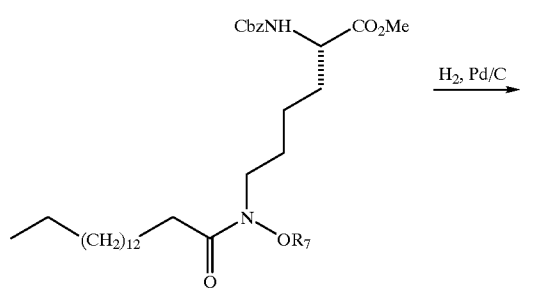
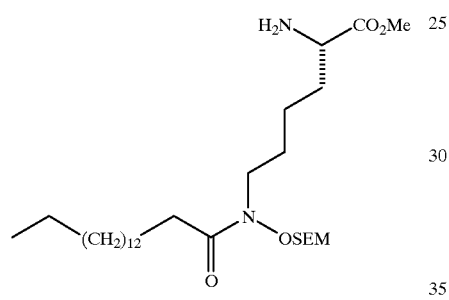
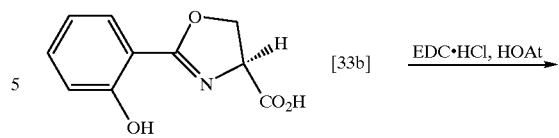
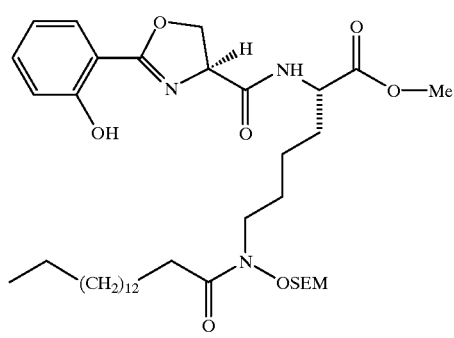
Reaction Scheme 3
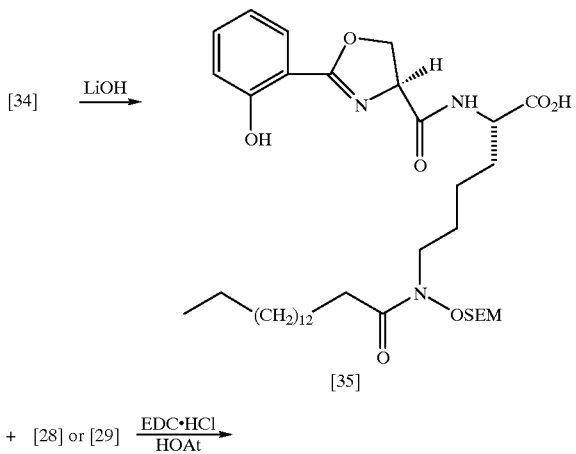
[35] + [28] or [29] →(EDC·HCl, HOAt)

-continued

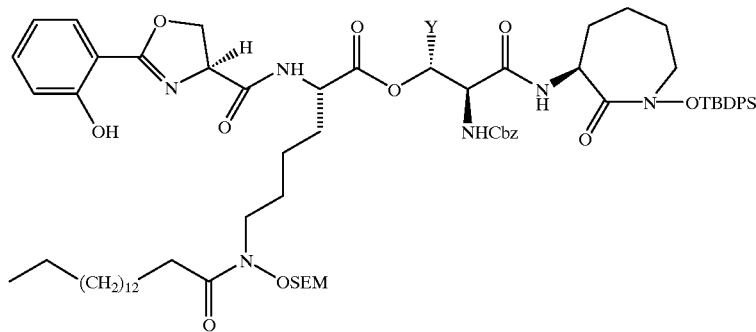

[36] Y = Me; [36a] Y = H

In the above reaction scheme SEM refers to [2-(trimethylsilyl)ethoxy]methyl and TBDPS refers to t-butyldiphenylsilyl protecting groups. Because of the difficulty in removing the protecting groups satisfactorily, a new approach to the preparation of the desired compound was found. The inefficiency of the reaction was attributed to competitive reactions associated with the partial ionization of the phenolic group of the 2-hydroxyphenyl group of the oxazoline portion of [35]. Taking advantage of the close $pK_a$ of about 9 for the phenolic and hydroxamate groups careful control of reaction acidity avoided ionization of the phenol and hydroxamate groups in the reactants with dramatic improvements in the formation of bonds via coupling by with the water soluble carbodiimide EDC.HCl in the presence of 1-hydroxy-7 azabenzotriazole (HOAt). The reaction when carried out with the above acidity control reagents and without protecting groups is shown in the following Reaction Scheme 4. The compound of the formula 1 [37] wherein Y is H was obtained in 81% yield while the compound wherein Y is methyl was obtained in 75% yield.

Reaction Scheme 4

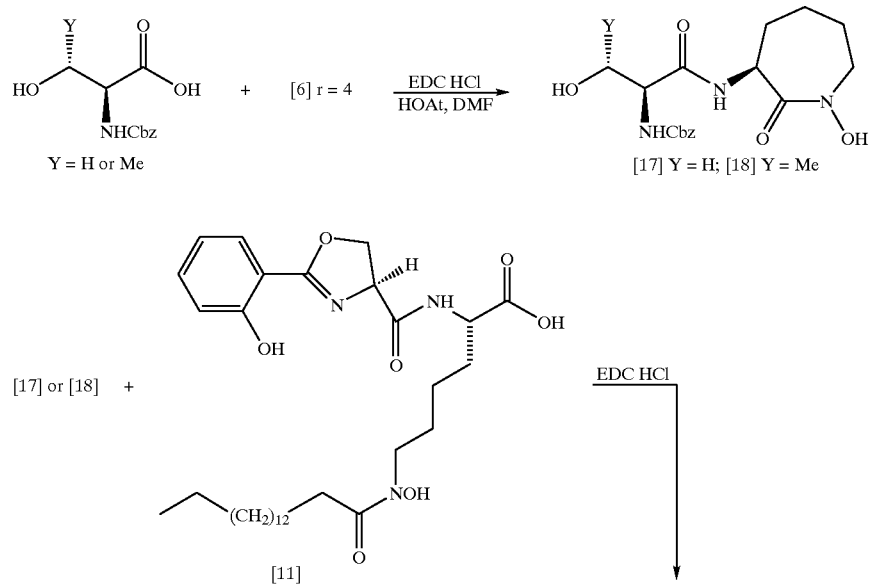

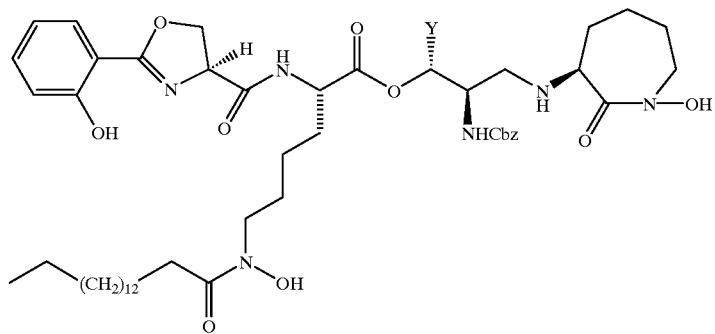
[37]
A further preferred compound of the invention [40a] where, in formula 1, X is O, $X_1$ is NH, Y and Z are H is prepared as shown below in Reaction Scheme 5.
An example of a compound of the invention where in the cobactin portion comprises a pyridin-2-one ring (formula 1 r=3) is represented by the following formula:
Reaction Scheme 5
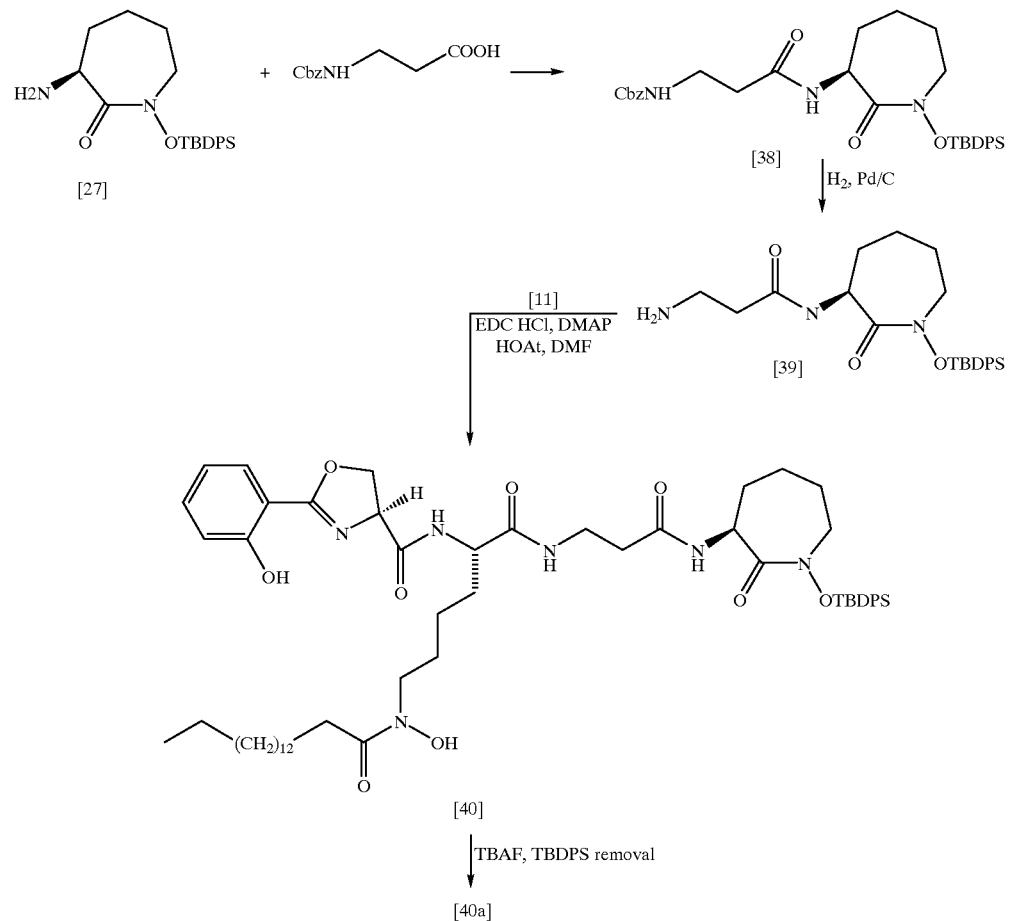

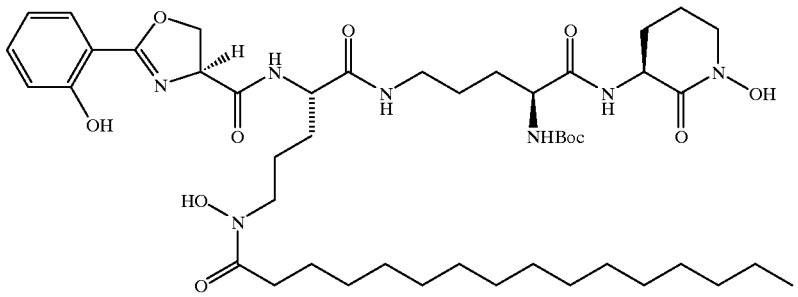
The compound is prepared by employing the coupling and deprotection procedures described in the foregoing reaction schemes.

According to the method provided by this invention *Mycobacterium tuberculosis* infections in man are treated by administering to the infected host an effective, non-toxic amount, of a compound represented by the formula 1 or a pharmaceutically acceptable non-toxic salt thereof. An effective amount of the compound of formula 1, in general, is between about 2 mg/kg of host body weight and about 25 mg/kg. The compound of formula 1 or a pharmaceutically acceptable salt thereof may be administered in a single daily dose or in multiple doses throughout the day. The amount administered and the particular dose regimen employed by the physician may vary depending on such factors as the severity of the disease, the duration of the infection prior to treatment, the age and general health of the infected host and the tolerance of the particular host to the treatment. The compound represented by the formula 1 or a pharmaceutically acceptable salt thereof may be administered parenterally or orally in a suitable pharmaceutical formulation. The route of administration may be determined by the acceptance of the dose regime by the individual host. Parenteral administration is achieved via im. injection or via iv. For such administration the compound or a salt thereof is formulated in a suitable diluent such as physiological saline, glucose or dextrose solution or Ringer's solution and the like. For iv. administration the drip method can be employed as well as the piggy back method wherein the drug formulation is added slowly to the host along with other fluids such as mineral solutions or nutrients such as glucose and amino acids. For oral administration a compound of the invention or a salt thereof can be formulated into gelatin capsules, e.g. in 250 mg and 500 mg doses, in tablet form or as a liquid solution or suspension.

The compounds represented by the formula [1] having basic or acidic groups form salts with mineral acids and organic acids and inorganic and organic bases respectively. For example when an $R_1$ substituent is a basic group such as an amino or substituted amino group salts can be formed with mineral acids such as hydrochloric, hydrobromic, sulfuric and phosphoric acids. Organic acids which can be used to form salts are e.g. the sulfonic acids such as methanesulfonic acid, benzenesulfonic acid and naphthylenesulfonic acids; benzoic acid, the chlorobenzoic acids, salicylic acid, malonic acid, maleic acid, succinic acid and like acids. Acidic groups e.g., when $R_1$ is a carboxy group, form salts with bases such as sodium hydroxide, potassium hydroxide, sodium carbonate, calcium hydroxide and ammonia, and with organic basis such as alkylamines, e.g. methylamine, t-butylamine, cyclohexylamine, dicyclohexylamine, abietylamine, diethanolamine, ethanolamine and like organic amines. Such salts are useful in the preparation of pharmaceutical formulations for administration of the compound represented by the formula 1. Such salts also can be useful in the isolation and purification of the compound represented by the formula [ 1].

The invention also provides pharmaceutical formulations for use in the above-described method. The formulations comprise a compound of the formula [1] or a pharmaceutically acceptable non-toxic salt thereof and a pharmaceutically acceptable carrier. Suitable carriers for im. or iv. administration include for example, deionized sterile water, physiological saline, 5% glucose and like commonly use carriers. Tablets may be formulated with the drug and binding agents, solubilizing agents, fillers and the like. Liquid suspensions which may be used can comprise the drug and water, a flavoring agent, solubilizing agent, coloring agent, a preservative and the like.

The pharmaceutical formulations provided herein may be made up in unit dosage form. For example, a formulation comprising 100 mg of the compound or a salt thereof and a pharmaceutically acceptable carrier. Other unit dosage formulations comprise 1 g of the drug or salt form thereof and a pharmaceutically acceptable carrier or 500 mg of the compound of formula 1 or a salt thereof and a pharmaceutically acceptable carrier. For im. administration the unit dose may be incorporated in sterile ampoules or vials while for iv. administration the unit dose may be provided in sterile bottles adaptable to hook up with tubing for the drip method with controls for regulating the rate of flow.

The following examples are provided to further illustrate the invention and are not to be construed as limitations thereon.

In the examples the following abbreviations have the indicated meanings:

FABMS—fast atom bombardment mass spec.
REIMS—high resolution electron impact mass spec.
DCC—dicyclocarbodiimide
EDC—ethyldimethylaminopropylcarbodiimide
DDQ—dichlorodicyanoquinone
HOAt—1-hydroxy-7-azabenzotriazole
THF—tetrahydrofuran
1*, 2* or 3* refers to once, twice or three times
DMAP—4-(dimethylamino)pyridine
TBDPS—t-butyldiphenylsilyl
SEM—[2-(trimethylsilyl)ethoxy]methyl
TBAF—tetrabutylammonium fluoride

PREPARATIONS

The following are the preparations of compounds used to make the compounds of the invention in the examples.

Bold numbers in parentheses adjacent to the title compounds in the preparations refer to the title compound of that preparation when used in other preparations and in the Examples. Bold numbers in brackets refer to the structures of compounds so numbered in the specification.

Preparation 1
2-(Benzyloxy)benzoic Acid

To a solution of salicylic acid (7 g, 0.05 mol) in methanol (100 mL) at −78° C., $SOCl_2$ (8 mL, 0.11 mol, 2.2 equiv.) was added dropwise. The reaction mixture was stirred at 40° C. overnight, concentrated and extracted with EtOAc. The organic layer was washed with $NaHCO_3$, brine, dried over $Na_2SO_4$, filtered and concentrated. The product methyl ester was then dissolved in DMF; BnBr (9 mL, 0.075 mol, 1.5 equiv.), $K_2CO_3$ (27.5 g, 0.2 mol, 4 equiv.) and NaI (75 mg) were added. The reaction mixture was stirred at room temperature for 12 h, diluted with EtOAc, washed with water, 0.5N HCl, and brine, dried over $Na_2SO_4$, filtered, concentrated and chromatographed on silica gel eluting with hexanes/EtOAc (10:1), to give the 2-benzyloxy methyl ester as an oil (6.8 g, 0.03 mol, 57%). To the benzyloxy ester was added KOH (3.2 g, 0.06 mol, 2 equiv.) and $THF/H_2O$ (1:1) (20 mL). The reaction mixture was stirred at room temperature overnight and extracted with EtOAc. The aqueous layer was acidified to pH=2 with 2N HCl and extracted with EtOAc. The combined organic layers were washed with brine, dried over $Na_2SO_4$, filtered and concentrated to afford 2-(benzyloxy)benzoic acid as white crystals (m=4.5 g, 70%).

Preparation 2
N-[2-(Benzyloxy)benzoyl]-L-Serine Benzyl Ester
Carbodiimide Method To a stirred solution of 2-(benzyloxy)benzoic acid (3.53 g, 15.5 mmol) and L-serine benzyl ester hydrochloride (3.27 g, 14 mmol) in $CH_2Cl_2$ (70 mL) was added $Et_3N$ (2.09 mL, 15 mmol) and 1-ethyl-3-(3-dimethylaminopropyl)carbodiimide (2.96 g, 15.5 mmol). After being stirred for 10 h at room temperature under argon, the reaction mixture was diluted with $CH_2Cl_2$ (200 mL), washed with $H_2O$, saturated $NaHCO_3$ solution, 5% citric acid aqueous solution, $H_2O$, brine, dried over $Na_2SO_4$, filtered, and concentrated. Recrystallization from toluene afforded the title compound (5.12 g, 90%), as white crystals: $R_f$=0.41 (EtOAc/$CH_2Cl_2$=1/5); mp 116–118° C.; $[a]^{23}D$=+24.1° (c=1.0, $CH_2Cl_2$); IR (KBr) 3500–3100, 1740, 1620 $cm^{-1}$; $^1H$ NMR (300 MHz, $CDCl_3$) δ8.81 (d, J=6.9 Hz, 1H, NH), 8.19 (dd, J1=7.8 Hz, J2=1.8 Hz, 1H, ArH), 7.46–7.25 (m, 11H, ArH), 7.10–7.04 (m, 2H, ArH), 5.21–5.11 [m, apparently 4 overlapping doublets, 4H, 2($CH_2Ph$)], 4.90–4.85 (m, 1H, CH), 3.93–3.89 (m, 2H, $CH_2OH$), 2.32 (br, 1H, OH); $^{13}C$ NMR (75 MHz, $CDCl_3$) δ(170.13, 165.56, 156.91, 135.50, 135.26, 133.17, 132.31, 128.74, 128.53, 128.33, 128.06, 127.99, 121.48, 121.09, 112.79, 71.23, 67.17, 63.61, 55.38; FABMS: 406 (M+1). Anal. calcd. for $C_{23}H_{21}NO_5$: C, 70.58; H, 5.41; N, 3.58, found: C, 70.43; H, 5.60; N, 3.37.

Preparation 3
Active Ester With Carbodiimide Method

To a stirred solution of 2-(Benzyloxy)benzoic acid (2.0 g, 8.7 mmol), L-serine benzyl ester hydrochloride (2.0 g, 8.7 mmol, 1 equiv.) and HOAt (1.2 g, 8.7 mmol, 1 equiv.) in DMF (200 mL) was added $Et_3N$ (0.98 mL, 9.6 mmol, 1.1 equiv.) and EDC. HCl (2.02 g, 4.8 mmol, 1.2 equiv.). After being stirred overnight at room temperature under nitrogen, the reaction mixture was diluted with EtOAc (200 mL), washed with 1 N HCl solution (60 mL), saturated $NaHCO_3$, saturated $NH_4Cl$ (60 mL), and brine (60 mL). The combined organic layers were dried over $Na_2SO_4$, filtered, concentrated and chromatographed on silica gel eluting with $CH_2Cl_2$/MeOH (95/5) to give amide N-[2-(benzyloxy)benzoyl]-L-serine benzyl ester (2.5 g, 70%) as white crystals. $R_f$=0.5 ($CH_2Cl_2$/MeOH=95/5); $^{11}H$ NMR (300 MHz, $CDCl_3$)δ8.80 (d,1H, NH), 8.19 (dd, 1H, ArH), 7.46–7.24 (m, 1H, ArH), 7.12–7.04 (m, 2H, ArH), 5.21–5.11 (m, 4H, 2($CH_2Ph$)), 4.91–4.87 (m, 1H, CH), 3.93–3.90 (m, 2H, $CH_2OH$), 2.2 (1H, OH).

Preparation 4
(S)-Benzyl 2-[2-(Benzyloxy)phenyl]-2-oxazoline-4-carboxylate (1)

To a stirred solution of N-[2-(benzyloxy)benzoyl]-L-serine benzyl ester (21) (545 mg, 1.35 mmol) in THF (10 mL) was added Burgess' reagent (methoxycarbonylsulfamoyltriethylammonium hydroxide, inner salt, 360 mg, 1.55 mmol, 1.1 equiv.). After being refluxed for 30 min at room temperature under argon, the reaction mixture was diluted with EtOAc (100 mL), washed with $H_2O$, brine, dried over $Na_2SO_4$, filtered, concentrated and chromatographed on silica gel eluting with EtOAc/$CH_2Cl_2$ (1/15) to yield oxazoline (1) (343 mg, 66%), as a white, amorphous solid: $R_f$=0.58 (EtOAc/$CH_2Cl_2$=1/15); mp 69–71° C. (recrystallized from EtOAc and hexanes); IR (KBr) 1732, 1630 $cm^{-1}$; $^1H$ NMR (300 MHz, $CDCl_3$) δ7.81 (dd, 1H, J1=7.8 Hz, J2=1.8 Hz, ArH), 7.50–7.47 (m, 2H, ArH), 7.42–7.26 (m, 9H, ArH), 7.00–6.96 (m, 2H, ArH), 5.28 (d, J=12.3 Hz, 1H, PhHH), 5.20 (d, J=11.7 Hz, 1H, PhHH), 5.18 (s, 2H, $CH_2Ph$), 5.00 (dd, J1=10.5 Hz, J2=8.1 Hz, 1H, $CHCH_2$), 4.68–4.52 (m, 2H, $CHCH_2$); $^{13}C$ NMR (75 MHz, $CDCl_3$)δ171.03, 165.65, 157.56, 136.79, 135.40, 132.64, 131.62, 128.50, 128.36, 128.29, 128.25, 127.53, 126.69, 120.67, 117.12, 113.75, 70.55, 69.16, 68.77, 67.12; FABMS: 388 (M+1); HREIMS calcd. for $C_{24}H_{21}NO_4$ 387.1471, found 387.1458.

Preparation 5
(S)-2-[2-(oxy)phenyl]-2-oxazoline-4-carboxylic Acid (2)

(S)-Benzyl 2-[2-(benzyloxy)phenyl]-2-oxazoline-4-carboxylate (1) (250 mg) was dissolved in methanol (20 mL). After purging with nitrogen gas for 30 min, the catalyst palladium on carbon (10%) (25 mg) was added. After being purged with $H_2$ gas for 30 min, the reaction mixture was stirred for 1 h under 1 atm $H_2$. The catalyst was then filtered on celite and the solvent was evaporated to afford the desired product in quantitative yield.

Preparation 6
(S)-2-[2-(Benzyloxy)phenyl]-2-oxazoline-4-carboxylic Acid (3)

To a mixture of benzyl ester (1) (25.7 mg, 0.0664 mmol) in 1:1 THF/$H_2O$ (3 mL) at 0° C. was added LiOH (9 mg, 0.348 mmol, 1.5 equiv.). The reaction mixture was stirred for 1 h at room temperature. The desired product (3) was obtained in 99% yield after purification by column chromatography ($CH_2Cl_2$/MeOH=85:15). FABMS: 298 (M+1); HREIMS calcd. for $C_{17}H_{15}NO_4$ 298.1079, found 298.1078.

Preparation 7
(S)-Methyl 2-[2-(Benzyloxy)phenyl]-2-oxazoline-4-carboxylate (4)

Compound (3) was esterified with methyl alcohol to provide (4).

Preparation 8
(S)-Methyl 2-[2-(oxy)phenyl]-2-oxazoline-4-carboxylate (5)

Oxazoline (4) (25 mg) was dissolved in methanol (3 mL). After purging with nitrogen gas for 30 min, the catalyst palladium on carbon (10%) (2.5 mg) was added. After being purged with $H_2$ gas for 30 min, the reaction mixture was stirred for 1.5 h under 1 atm $H_2$. The catalyst was then filtered through a pad of celite and the solvent was evaporated to afford the desired product (5) in 95% yield.

Preparation 9
(S)-Isopropyl 2-[2-(Benzyloxy)phenyl]-2-oxazoline-4-carboxylate (6)

2-(Benzyloxy) benzoic acid (190.93 g, 0.048 mol) and L-serine isopropyl ester hydrochloride (8.8 g, 0.048 mol) were placed in $CH_2Cl_2$ (250 mL) and cooled on ice. $Et_3N$ (6.66 mL, 0.048 mol) was added, followed by DCC (12.38 g, 0.06 mol). The solution was stirred at 0° C. for 1 h and then at room temperature for 3 h. The mixture was concentrated to 140 mL, chilled and filtered. The filtrate was washed twice with 5% $Na_2CO_3$ and once with 0.5 N HCl. Excess DCC was destroyed by stirring with HOAc (0.5 mL) and $H_2O$ (10 mL) for 20 min and then filtering. The solvent was dried ($MgSO_4$), chilled and refiltered. Evaporation of solvent left 14.5 g (85%) of L-N-[2-(benzyloxy)benzoyl]-L-serine isopropyl ester as an oil. Some of this oil (9.15 g, 25.6 mmol) was dissolved in ether (150 mL) and chilled on ice. $SOCl_2$ (5.5 mL) was added such that the temperature remained below 5° C. After stirring at 0° C. for 100 min, more $SOCl_2$ (3 mL) was added. Two more portions of $SOCl_2$ (each 3 mL) were added in 100 min intervals. Then the reaction mixture was left at −20° C. overnight. The resulting crystals were collected by centrifugation at 4° C. and washed by suspending in ice-cold ether and recentrifuging. The supernatant was returned to the freezer. The crystals were distributed between 10% $Na_2CO_3$ and ether. The ether layer was washed with 10% $Na_2CO_3$, dried ($MgSO_4$) and evaporated to leave 4.812 g of needles. A further 1.006 g of the oxazoline was obtained from the supernatant after 24 more hours at −20° C., with the same workup as above. Total yield: 5.818 g (67%); mp (ether/hexanes) 61–62° C.; $^1H$ NMR δ7.7–8.0 (m, 1H), 7.2–7.7 (m, 6H), 6.8–7.2 (m, 2H), 5.2 (s, 2H), 5.0 (m, 1H), 4.6 (m, 3H), 1.3 (d, 6H).

Preparation 10
(S)-Benzyl 2-[2-(Benzyloxy)phenyl]-2-thiazoline-4-carboxylate (7)

N-[2-(Benzyloxy)benzoyl]-L-serine benzyl ester (20 mg, 0.05 mmol) and Lawesson's reagent [2,4-bis(p-methoxyphenyl)-1,3-dithiadiphosphetane-2,4-disulfide] (20 mg, 0.05 mmol, 1 equiv.) were dissolved in toluene (15 mL). After being refluxed overnight under nitrogen, the reaction mixture was diluted with EtOAc (20 mL), washed with brine, dried over $MgSO_4$, filtered, concentrated and chromatographed on silica gel eluting with hexanes/EtOAc (6/1) to yield thiazoline (7) as a clear oil. $R_f$=0.3 (hexanes/EtOAc, 6:1); $^1H$ NMR (300 MHz, $CDCl_3$) δ8.00 (dd, 1H, ArH), 7.51–7.49 (m, 2H, ArH), 7.42–7.25 (m, 9H, ArH), 7.02–6.95 (m, 2H, ArH), 5.28 (d, 1H, PhCHH), 5.20 (d, 1H, PhCHH), 5.18 (s, 2H, $CH_2Ph$), 5.12 (dd, 1H, $CHCH_2$), 3.60–3.47 (m, 2H, $CHCH_2$); MS (FAB) m/z 404 MH$^+$, measured exact mass: 404.1313, calculated exact mass: 404.1320.

Preparation 11
Benzyl 2-[2-(Benzyloxy)phenyl]-2-oxazoline-4-methyl-4-carboxylate (8)

Oxazoline (1) (1 g, 2.6 mmol) dissolved in freshly distilled THF (30 mL) was cooled at 78° C. After addition of methyl iodide (1.83 g, 800(μL, 13 mmol, 5 equiv.) and stirring at 78° C. for 10 min, sodium dimethylsilylamide (1M in THF) (4 mmol, 4 mL, 1.5 equiv) was added slowly via a syringe. After stirring at for 45 min, a few drops of water were added to the reaction mixture which was then allowed to warm up to room temperature. The THF was evaporated and the residue was taken-up in $EtOAc/H_2O$. The aqueous layer was re-extracted with EtOAc and the combined organic layers were washed with brine, dried over sodium sulfate, filtered and concentrated. Purification of the crude by column chromatography (hexanes/EtOAc=4/1) afforded the racemic desired product (8) as a colorless oil (0.810 g, 78%). $R_f$=0.58 (hexanes/EtOAc=4/1) $^1H$ NMR (300 MHz, $CDCl_3$) δ7.70–5.95 (m, 16H, ArH), 5.30–5.20 (q, 2H, $CH_2Ph$), 5.20 (s, 2H, $CH_2Ph$), 4.85 (d, 1H, CHH), 4.20 (d, 1H, CHH), 1.65(s, 3H, $CH_3$).

Preparation 12
(S) 2-[2-(Benzyloxy)phenyl]-2-oxazoline-4-methyl-4-carboxylic Acid (9)

To a solution of oxazoline (8) (180 mg, 0.45 mmol) dissolved in THF/Water (1:1) (6 mL) was added potassium hydroxide (51 mg, 0.9 mmol, 2 equiv.). After being stirred overnight at room temperature, the reaction mixture was extracted with EtOAc. The aqueous layer was acidified with 1N HCl and re-extracted with EtOAc. The combined organic layers were washed with brine, dried over sodium sulfate, filtered and concentrated to afford the desired product in 65% yield (91.4 mg) as a clear oil. $^1H$ NMR (300 MHz, $CDCl_3$) δ7.65 (d, 1H, ArH), 7.40 (m, 1H, ArH), 7.05 (d, 1H, ArH), 6.90 (t, 1H, ArH), 4.85 (d, 1H, CHH), 4.20 (d, 1H, CHH), 1.65(s, 3H, $CH_3$).

Preparation 13
(S) 2-[2-(Oxy)phenyl]-2-oxazoline-4-methyl-4-carboxylic Acid (10)

Oxazoline (8) (30 mg, 0.075 mmol) was dissolved in methanol (4 mL). After purging with nitrogen gas for 30 min, the catalyst palladium on carbon (10%) (4 mg) was added. After being purged with $H_2$ gas for 30 min, the reaction mixture was stirred for 1.5 h under 1 atm $H_2$. The catalyst was then filtered off on celite and the solvent evaporated to afford the desired product (10) in 94% yield. $R_f$=0.20 (Methanol/EtOAc=1/9).

Preparation 14
(S)-Benzyl 2-[2-(Benzyloxy)phenyl]-2-oxazoline-5-methyl-4-carboxylate (11)

To a stirred solution of N-[2-(benzyloxy)benzoyl]-L-threonine benzyl ester (409 mg, 0.976 mmol) in THF (20 mL) was added Burgess' reagent (methoxycarbonylsulfamoyltriethylammonium hydroxide, inner salt,) 350 mg, 1.46 mmol, 1.5 equiv.). After being stirred at room temperature under nitrogen overnight and refluxed for 1 h, the reaction mixture was diluted with EtOAc, washed with $NH_4Cl$, brine, dried over $Na_2SO_4$, filtered, concentrated, and chromatographed on silica gel eluting with $EtOAc/CH_2Cl_2$ (1/15) to yield oxazoline (11) (76%). $^{13}C$ NMR (600 MHz, $CDCl_3$) δ169.768, 165.810, 157,604, 136.811, 135.341, 132.532, 131.625, 128.566, 128.566, 128.486, 128.350, 128.278, 127.550, 126.874, 120.668, 117,574, 113.677, 77.398, 71.552, 70.617, 66.768, 16.047; FABMS: 402 (M+1); calculated exact mass (M+1): 402.1705, measured exact mass (M+1): 402.1717.

Preparation 15
(S)-Methyl 2-[2-(Benzyloxy)phenyl]-2-oxazoline-5-methyl-4-carboxylate (12)

To a stirred solution of N-[2-(benzyloxy)benzoyl]-L-threonine methyl ester (31 mg, 0.09 mmol) in THF (2 mL) was added Burgess' reagent (methoxycarbonylsulfamoyltriethylammonium hydroxide, inner salt), 32.3 mg, 0.14 mmol, 1.5 equiv.). After being stirred at room temperature under nitrogen overnight and refluxed for 1 h, the reaction mixture was diluted with EtOAc, washed with NH$_4$Cl, brine, dried over Na$_2$SO$_4$, filtered, concentrated, and chromatographed on silica gel eluting with EtOAc/CH$_2$Cl$_2$ (1/15) to yield oxazoline (12) (80.5%). $^{13}$C NMR (600 MHz, CDCl$_3$) δ170.432, 165.713, 157.601, 136.804, 132.551, 131.590, 128.269, 127.579, 126.899, 120.656, 117.542, 113.570, 77.737, 71.692, 70.581, 51.953, 16.108; FABMS: 326 (M+1); calculated exact mass (M+1): 326.1392, measured exact mass (M+1): 326.1383.

Preparation 16
(S) 2-[2-(Oxy)phenyl]-2-oxazoline-5-methyl-4-carboxylic Acid (13)

Oxazoline (11) (50 mg) was dissolved in methanol (5 mL). After purging with nitrogen gas for 30 min, the catalyst palladium on carbon (10%) (5 mg) was added. After being purged with H$_2$ gas for 30 min, the reaction mixture was stirred for 1.5 h under 1 atm H$_2$. The catalyst was then filtered off on celite and the solvent evaporated to afford the desired product (13) in 99% yield. $^{13}$C NMR (600 MHz, CDCl$_3$) δ171.611, 167.442, 159.871, 134.152, 128.152, 128.412, 118.743, 116.752, 109.809, 77.628, 69.690, 49.276, 15.913; FABMS: 222 (M+1); calculated exact mass (M+1): 222.0766, measured exact mass (M+1): 222.0768.

Preparation 17
(S)-Benzyl 2-[2-(Benzyloxy)phenyl]-2-thiazoline-5-methyl-4-carboxylate (14)

N-[2-(Benzyloxy)benzoyl]-L-threonine benzyl ester (50 mg, 0.119 mmol) and Lawesson's reagent (2,4-bis(p-methoxyphenyl)-1,3-dithiadiphosphetane-2,4-disulfide) (24 mg, 0.06 mmol, 0.5 equiv.) were dissolved in toluene (2.5 mL). After being refluxed under nitrogen, the reaction mixture was diluted with EtOAc, washed with brine, dried over MgSO$_4$, filtered, concentrated and chromatographed on silica gel eluting with hexane/EtOAc (6/1) to yield thiazoline (14) in 40% yield. $^1$H NMR (300 MHz, CDCl$_3$) δ7.95 (dd,1H, ArH), 7.51–7.49 (d, 2H, ArH), 7.45–7.25 (m, 9H, ArH), 7.05–6.95 (m, 2H, ArH), 5.24 (s, 2H, CH$_2$Ph), 5.19 (s, 2H, CH$_2$Ph), 4.82 (d, 1H, CH), 4.20 (p, 1H, CH), 1.25 (d, 3H, CH$_3$); FABMS: 418 (M+1); calculated exact mass (M+1): 418.1477, measured exact mass (M+1): 418.1472.

Preparation 18
Benzyl 2-[2-(Benzyloxy)phenyl)]-2-oxazole-4-carboxylate (15)

Oxazoline (1) (40.7 mg, 0.105 mmol) and DDQ (26.3 mg, 0.116 mmol, 1.1 equiv.) were dissolved in benzene (3 mL). The reaction mixture was refluxed for 2 h, cooled at room temperature and then diluted with CH$_2$Cl$_2$. It was washed with 2N NaOH, NH$_4$Cl, brine, dried over Na$_2$SO$_4$, filtered, concentrated and chromatographed on silica gel eluting with CH$_2$Cl$_2$/MeOH (95/5) to yield oxazole (15) in 80.5% yield. R$_f$=0.33 (CH$_2$Cl$_2$/MeOH=95/5). $^1$H NMR (300 MHz, CDCl$_3$) δ8.30 (s,1H, CH), 8.05 (dd, 1H, ArH), 7.55–7.25 (m, 11H, ArH), 7.10–7.05 (t, 2H, ArH), 5.40 (s, 2H, PhCH$_2$), 5.20 (s, 2H, PhCH$_2$).

Preparation 19
Methyl 2-[2-(Benzyloxy)phenyl]-2-oxazole-5-methyl-4-carboxylate (16)

Oxazoline (12) (717 mg, 2.21 mmol) and DDQ (551 mg, 2.43 mmol, 1.1 equiv.) were dissolved in benzene (35 mL). The reaction mixture was refluxed for 2 h, cooled at room temperature and then diluted with EtOAc (100 mL). It was washed with 2N NaOH (2*20 mL), 0.5 HCl (1*20 mL), brine 3*20 mL), dried over Na$_2$SO$_4$, filtered, concentrated and chromatographed on silica gel eluting with hexane/EtOAc (3/1) to yield oxazole (16) as a white solid in 86% yield, mp=78.5–79.5° C. R$_f$=0.1 (hexanes/EtOAc=3/1). $^1$H NMR (300 MHz, CDCl$_3$) δ8.02 (dd, 1H, ArH), 7.56 (d, 2H, ArH), 7.42–7.26 (m, 4H, ArH), 7.06–7.00 (m, 2H, ArH), 5.20 (s, 2H, CH$_2$Ph), 3.95 (s, 3H, CO$_2$CH$_3$), 2.65 (s, 3H, CH$_3$); $^{13}$C NMR (600 MHz, CDCl$_3$) δ162.931, 158.468, 156.603, 156.069, 136.657, 131.953, 130.617, 128.271, 127.997, 127.610, 126.694, 120.874, 116.304, 113.330, 70.358, 51.755, 11.937. HEIMS: 323 (M); calculated exact mass: 323.1158, measured exact mass: 323.1176.

Preparation 20
2-[2-(Benzyloxy)phenyl]-2-oxazole-5-methyl-4-carboxylic Acid (17)

To a mixture of methyl ester (16) (75 mg, 0.232 mmol) in 1:1 THF/H$_2$O (5 mL) at 0° C. was added LiOH (9 mg, 0.348 mmol, 1.5 equiv.). The reaction mixture was stirred for 30 min at 0° C. and then was allowed to warm-up to room temperature. The desired oxazole (17) was obtained in 98% yield as a white solid. $^1$H NMR (300 MHz, CDCl$_3$) δ10.17 (s, 1H, OH), 8.04 (dd, 1H, ArH), 7.60–7.54 (d, 2H, ArH), 7.46–7.26 (m, 4H, ArH), 7.10–7.02 (m, 2H, ArH), 5.21 (s, 2H, CH$_2$Ph), 2.70 (s, 3H, CH$_3$). $^{13}$C NMR (300 MHz, CDCl$_3$) δ166.399, 158.595, 157.118, 156.697, 136.611, 132.221, 130.624, 128.398, 127.724, 127.657, 126.781, 121.001, 116.030, 113.437, 70.478, 12.15; FABMS: 310 (M+1); calculated exact mass (M+1): 310.1079, measured exact mass (M+1): 310.1063.

Preparation 21
2-[2-(Oxy)phenyl]-2-oxazole-5-methyl-4-carboxylic Acid (18)

Oxazole (17) (0.838 mmol) was dissolved in methanol (15 mL). After purging with nitrogen gas for 30 min, the catalyst palladium on carbon (10%) (45 mg) was added. After being purged with H$_2$ gas for 30 min, the reaction mixture was stirred for 6 h under 1 atm H$_2$. The catalyst was then filtered off through a pad of celite and the solvent evaporated to afford the desired product 18. $^1$H NMR (300 MHz, CDCl$_3$) δ7.60 (d, 1H, ArH), 7.20–7.10 (td, 1H, ArH), 6.80 (d, 1H,ArH), 6.73 (t, 1H, ArH), 4.45 (1H, OH), 2.50 (s, 3H, CH$_3$). $^{13}$C NMR (300 MHz, CDCl$_3$) δ163.185, 158.762, 156.470, 154.899, 132.241, 126.915, 125.665, 119.170, 116.691, 109.936, 11.349.

Preparation 22
TBDPS-Protected Cobactin [29]

To a solution of 21 mg of the TBDPS protected azepine-2-one amine [6 r=4] (0.055 mmol), 12.5 mg of Cbz protected threonine (0.05 mmol), 1.0 equiv of HOAt (6.8 mg, 0.05 mmol) and 7 mg of DMAP (0.03 mmol) in 0.5 mL of dry DMF, a pre-mixed solution of 0.055 mmol of EDC.HCl and 0.055 mmol of DMAP in 0.5 mL of dry DMF was added dropwise. The resulting mixture was allowed to stand at room temperature for 3 h. The reaction mixture was then diluted with 15 mL of EtOAc and washed with water (1×5 mL), brine (2×5 mL), dried over Na$_2$SO$_4$, filtered and concentrated. The residue was purified by silica chromatography with 1:1 ethyl acetate/hexanes as the eluent to afford 27.3 mg (88%) of [29] as a colorless oil: R$_f$=0.27 (1:1 EtOAc/hexanes); IR (neat) 3315, 2950, 2865, 1735, 1530, 1456 cm$^{-1}$; $^1$H NMR (300 MHz, CDCl$_3$) δ7.74–7.70 (m, 5H), 7.46–7.33 (m, 10H), 7.04 (bd, 1H), 5.63 (bd, 1H), 5.11 (s, 2H), 4.28–4.06 (m, 3H), 3.58–3.41 (m, 2H), 3.30 (bs, 1H), 1.30–1.98 (m, 6H), 1.14 (s, 9H), 1.09 (d, 3H, J=6.3 Hz);

$^{13}$C NMR (125 MHz, CDCl$_3$) δ169.71, 169.38, 156.30, 136.15, 136.06, 132.01, 131.52, 130.27, 130.24, 128.52, 128.15, 128.04, 127.61, 127.53, 76.51, 67.51, 67.08, 58.51, 54.16, 30.53, 27.26, 26.89, 25.29, 19.57, 18.14; HRFABMS calcd. for C$_{34}$H$_{44}$N$_3$O$_6$Si 618.2999, found 618.3025.

Preparation 23
TBDPS-Protected Cobactin [128]

To a solution of 17 mg of amine [27] (0.045 mmol), 9.6 mg of Cbz protected serine (0.04 mmol), 1.0 equiv of HOAt (5.4 mg, 0.04 mmol) and 5.5 mg. of DMAP (0.045 mmol) in 0.5 mL of dry DMF, a pre-mixed solution of 0.045 mmol of EDC.HCl and 0.045 mmol of DMAP (5.5 mg) in 0.5 mL of dry DMF was added dropwise. The resulting mixture was allowed to stand at the room temperature for 3 h. The reaction mixture was then diluted with 10 mL of EtOAc and washed with water (1×5 mL), brine (2×5 mL), dried over Na$_2$SO$_4$, filtered and concentrated. The residue was purified by silica chromatography with 3:1 ethyl acetate/hexanes as the eluent to afford 21.6 mg (90%) of [28] as a colorless oil: R$_f$=0.40 (3:1 EtOAc/hexanes); IR (neat) 3315, 2940, 2862, 1725, 1535, 1455 cm$^{-1}$ ; $^1$H NMR (300 MHz, CDCl$_3$) δ7.72 (m, 5H), 7.47–7.30 (m, 10H), 6.83 (bd, 1H), 5.65 (bd, 1H), 5.11 (s, 2H), 4.30 (m, 2H), 4.20 (m, 1H), 3.89 (dd, 1H, J=6.6, 2.2 Hz), 3.56–3.51 (m, 1H), 3.49–3.42 (m, 1H), 1.81–1.74 (m, 3H), 1.59–1.51 (m, 3H), 1.45–1.41 (m, 1H), 1.13 (s, 9H); $^{13}$C NMR (125 MHz, CDCl$_3$) δ169.82, 169.21, 155.92, 136.74, 135.40, 131.96, 131.51, 129.59, 127.90, 127.50, 126.96, 76.40, 67.09, 65.89, 64.57, 63.44, 54.96, 28.35, 27.56, 26.32, 19.56; HRFABMS calcd. for C$_{33}$H$_{42}$N$_3$O$_6$Si 604.2843, found 604.2823.

Preparation 24
SEM-Protected Hydroxamate [32]

To a solution of 78 mg of [30] (0.25 mmol), 169 mg of NaHCO$_3$ (2.01 mmol) in 8 mL of dry CH$_2$Cl$_2$, 4 equiv of palmitoyl chloride (0.30 mL) was added dropwise. The resulting solution was then allowed to stand at room temperature for 14 h. The mixture was diluted with 20 mL of EtOAc and washed with 1N HCl (3×5 mL), brine (3×5 mL), dried over Na$_2$SO$_4$, filtered and concentrated. The residue was then taken up in 25 mL of 6% Hünig's base in methanol. The resulting mixture was then allowed to stand at room temperature for 12 h. The mixture was concentrated. The residue was transferred to a solution of 0.87 mL of Hünig's base (5.0 mmol) and 20 mg of DMAP in 5 mL of toluene, followed by addition of 10 equiv of SEMCl (0.44 mL, 2.5 mmol) dropwise. The resulting solution was then allowed to stand at 65° C. overnight under argon. The mixture was cooled to room temperature and diluted with 20 mL of EtOAc. Then the mixture was washed with 1N HCl (2×10 mL), saturated aqueous NaHCO$_3$ (2×10 mL), brine (2×10 mL) and dried over Na$_2$SO$_4$, filtered and concentrated. The residue was purified by silica chromatography with 1:15 ethyl acetate/hexanes as the eluent to afford 162 mg (96%) of [32] as a colorless oil: R$_f$=0.21 (1:15 EtOAc/hexanes); IR (neat) 3312, 2910, 2822, 1722, 1650 cm$^{-1}$; $^1$H NMR (300 MHz, CDCl$_3$) δ7.36–7.31(m, 5H), 5.36 (d, J=7.8 Hz, 1H), 5.10 (s, 2H), 4.90 (s, 2H), 4.37–4.30 (m, 1H), 3.76–3.61 (m, 7H), 2.38 (t, J=7.6 Hz, 2H), 1.86–1.03 (m, 32H), 0.99–0.93 (m, 2H), 0.88 (t, J=6.7 Hz, 3H), 0.03 (s, 9H); $^{13}$C NMR (125 MHz, CDCl$_3$) δ175.36, 172.69, 155.82, 136.18, 128.29, 127.89, 127.85, 99.08, 67.38, 66.68, 53.64, 52.09, 47.16, 32.43, 31.75, 29.52, 29.49, 29.38, 29.30, 29.27, 29.19, 26.10, 24.33, 22.52, 22.14, 18.02, 13.96, -1.63; HRFABMS calcd. for C$_{37}$H$_{67}$N$_2$O$_7$Si 679.4717, found 679.4702.

Preparation 25
Oxazoline-Hydroxamate [34]

A solution of 670 mg of [33] (0.99 mmol) in 25 mL of MeOH, was purged with argon for 15 min. Then 70 mg of 10% Pd—C was added and the system was flushed with argon for another 10 min. The resulting slurry was stirred under H$_2$ (1 atm) for 3 h. After filtering off the catalyst through a pad of Celite, the solvent was removed under vacuum to provide the corresponding free amine. The amine was then treated with 202 mg of oxazoline derivative 2-[2-(oxy)phenyl]-2-oxazoline-3-carboxylic acid (2) (0.98 mmol) in the presence of 187 mg of EDC.HCl (0.98 mmol), 133 mg of HOAt (0.98 mmol) and 25 mg of DMAP in 30 mL of dry DMF. The resulting solution was allowed to stand at room temperature for 3 h. The mixture was diluted with 60 mL of EtOAc. The organic layer was washed with 1N HCl (2×10 mL), saturated aqueous NaHCO$_3$ (2×10 mL), brine (2×10 mL) and dried over NaSO$_4$, filtered and concentrated. The residue was purified by silica chromatography with 1:1 ethyl acetate/hexanes as the eluent to afford 660 mg (91%) of [34] as a colorless oil: R$_f$=0.40 (1:1 EtOAc/hexanes); IR (neat) 3290, 2910, 2820, 1740, 1650, 1630 cm$^{-1}$; $^1$H NMR (300 MHz, CDCl$_3$) δ7.67 (dd, J=7.9, 1.7 Hz, 1H), 7.39 (ddd, J=8.7, 7.5, 1.7 Hz, 1H), 7.00 (dd, J=8.5, 0.8 Hz, 1H), 6.93–6.85 (m, 1H), 4.94 (t, J=9.6 Hz, 1H), 4.84 (s, 2H), 4.65–4.61 (m, 2H), 4.57–4.50 (m, 1H), 3.73 (s, 3H), 3.72–3.66 (m, 2H), 3.60 (t, J=7.1 Hz, 2H), 2.33 (d, J=7.6 Hz, 2H), 1.91–1.52 (m, 6H), 1.28–1.16 (m, 26H), 0.95–0.89 (m, 2H), 0.83 (t, J=6.8 Hz, 3H), -0.03 (s, 9H); $^{13}$C NMR (75 MHz, CDCl$_3$) δ175.45, 172.09, 170.27, 167.68, 159.72, 134.13, 128.47, 118.95, 116.88, 109.94, 99.13, 69.40, 67.97, 67.47, 52.37, 52.04, 47.29, 32.50, 31.82, 31.58, 29.59, 29.56, 29.44, 29.37, 29.26, 26.18, 24.42, 22.59, 22.35, 18.08, 14.02, -1.56; HRFABMS calcd. for C$_{39}$H$_{68}$N$_3$O$_8$Si 734.4775, found 734.4764.

EXAMPLE 1
Protected Mycobactin [36]

To a solution of 66 mg of amine [27] (0.173 mmol), 41 mg of Cbz protected threonine (0.173 mmol), 1.2 equiv of HOAt (21 mg, 0.210 mmol) and 21 mg of DMAP (0.173 mmol) in 1.0 mL of dry DMF, a pre-mixed solution of 0.21 mmol of EDC (40 mg) and 0.173 mmol of DMAP (21 mg) in 0.5 mL of dry DMF was added dropwise. After standing at room temperature for 3 h, the mixture was charged with 119 mg of acid [35] (0.165 mmol) and 25 mg of EDC.HCl (0.13 mmol). The resulting solution was heated at 55° C. for 42 h before it was cooled to room temperature. The reaction mixture was then diluted with 10 mL of EtOAc and washed with water (3×5 mL), brine (3×5 mL), dried over Na$_2$SO$_4$, filtered and concentrated. The residue was purified by silica chromatography with 3:1 ethyl acetate/hexanes as the solvent system to afford 151.5 mg (85%) of [36] as a colorless oil: IR (neat) 3405, 2960, 2925, 1790, 1725, 1705, 1660 cm$^{-1}$; $^1$H NMR (500 MHz, CDCl$_3$) δ11.23 (bs, 1H), 7.68 (td, 1H, J=8.1, 1.5 Hz), 7.52 (m, 1H), 7.44–7.13 (m, 6H), 7.01 (d, 1H, J=8.1 Hz), 6.91–6.86 (m, 1H), 5.77–5.75 (m, 1H), 5.12, 5.09 (ABq, 2H, J=9.9 Hz), 5.01–4.82 (m, 1H), 4.92 (s, 1H), 4.87 (s, 1H), 4.68–4.54 (m, 4H), 4.25–4.19 (m, 2H), 3.92–3.46 (m, 6H), 2.43–2.34 (m, 2H), 2.05–1.24 (m, 41H), 1.13 (t, 2H, J=6.9 Hz), 0.99–0.91 (m, 2H), 0.87 (t, 3H, J=6.3 Hz), 0.02 (s, 9H); $^{13}$C NMR (150 MHz, CDCl$_3$) δ175.81, 170.72, 169.82, 169.13, 168.96, 167.55, 159.62, 156.53, 136.17, 134.11, 128.47, 128.40, 128.01, 127.98, 127.91, 118.92, 116.87, 109.95, 99.10, 69.06, 67.83, 67.54, 67.29, 67.01, 58.66, 53.00, 52.00, 50.97, 32.51, 31.83, 30.89, 30.77, 30.65, 29.61, 29.60, 29.58, 29.56, 29.47, 29.43, 29.38, 27.67, 27.48, 26.09, 25.82, 24.45, 22.60, 22.37, 22.16, 18.33, 18.08, 14.04, -1.47; HRFABMS calcd. for C$_{56}$H$_{89}$N$_6$O$_{13}$Si 1081.6257, found 1081.6227.

EXAMPLE 2

Protected Mycobactin [36a]

To a solution of 33 mg of amine [27] (0.086 mmol), 21 mg of Cbz protected serine (0.086 mmol), 1.0 equiv of HOAt (12 mg, 0.086 mmol) and 13 mg of DMAP (0.045 mmol) in 1.0 mL of dry DMF, a pre-mixed solution of 0.10 mmol of EDC.HCl and 0.10 mmol of DMAP (12.2 mg) in 0.5 mL of dry DMF was added dropwise. After standing at room temperature for 3 h, the mixture was charged with 62 mg of acid [35] (0.086 mmol) and 19 mg of EDC.HCl (0.10 mmol). The resulting solution was heated at 55° C. for 30 h before it was cooled to room temperature. The reaction mixture was then diluted with 10 mL of EtOAc and washed with water (3×5 mL), brine (3×5 mL), dried over $Na_2SO_4$, filtered and concentrated. The residue was purified by silica chromatography with 3:1 ethyl acetate/hexanes as the eluent to afford 83.3 mg (91%) of [36a] as a colorless oil: IR (neat) 3430, 2975, 2940, 1740, 1730, 1655 $cm^{-1}$; $^1H$ NMR (500 MHz, $CDCl_3$) δ11.31 (bs, 1H), 7.68 (d, 1H, J=8.0 Hz), 7.54 (dd, 1H, J=12.5, 6.5 Hz), 7.42–7.29 (m, 5H), 7.24–7.22 (m, 1H), 7.16 (bd, 1H), 7.00 (d, 1H, J=8.5 Hz), 6.89 (dt, 1H, J=7.5, 2.5 Hz), 5.78 (m, 1H), 5.12, 5.09 (ABq, 2H, J=16.0 Hz), 4.96 (m, 1H), 4.92 (s, 1H), 4.87 (s, 1H), 4.65–4.55 (m, 4H), 4.28–4.25 (m, 1H), 4.22 (dd, 1H, J=16.5, 6.5 Hz), 3.96–3.81 (m, 1H), 3.76–3.64 (m, 4H), 3.57–3.54 (m, 1H), 2.41 (t, 1H, J=7.5 Hz), 2.37 (t, 1H, J=7.5 Hz), 2.03–1.23 (m, 38H), 1.13 (dd, 2H, J=12.0, 6.5 Hz), 0.98–0.92 (m, 2H), 0.87 (t, 3H, J=6.5 Hz), 0.02 (s, 9H); $^{13}C$ NMR (125 MHz, $CDCl_3$) δ175.78, 170.88, 170.73, 167.88, 167.62, 166.84, 159.48, 155.55, 136.07, 134.05, 128.57, 128.52, 128.20, 128.15, 128.08, 119.09, 116.93, 110.32, 99.21, 69.26, 67.66, 67.15, 64.54, 53.44, 52.78, 52.35, 51.24, 50.75, 32.62, 31.91, 31.89, 31.23, 30.87, 29.66, 29.56, 29.48, 29.45, 29.35, 29.33, 27.60, 26.12, 25.70, 25.54, 24.61, 22.68, 22.65, 22.59, 22.36, 18.18, 14.12, −1.47; HRFABMS calcd. for $C_{55}H_{86}N_6O_{13}Si$ 1067.6100, found 1067.6104.

EXAMPLE 3

Mycobactin [11] Methyl Ester

A slurry of 880 mg of protected amine [31] (1.61 mmol) with 200 mg of 10% Pd—C in 20 mL of MeOH was purged with a $N_2$ stream for 10 min and subsequently with $H_2$ for an additional 15 min. The reaction mixture was stirred under $H_2$ (1 atm) at room temperature for 3 h. to remove the Cbz protecting group. Then the palladium catalyst was filtered off through a pad of Celite. The solution was concentrated to yield the corresponding free amine. Without further purification, the crude amine was dissolved in a 20 mL of fresh distilled DMF solution containing 330 mg of 2-[2-(oxy)phenyl}-2-oxazoline-4-carboxylic acid (2) (1.59 mmol) and 217 mg of HOAt (1.59 mmol). To above solution, 336 mg of EDC.HCl (1.75 mmol) was added. The resulting solution was allowed to stand at room temperature for 3 h before it was diluted with 60 mL of EtOAc and 10 mL of 1N HCl. The organic layer was washed with 0.5N HCl (2×10 mL), 5% ascorbic acid (1×10 mL), saturated aqueous $NaHCO_3$ (1×10 mL), brine (2×10 mL), dried over $Na_2SO_4$, filtered and concentrated. The residue was purified silica chromatography with 1:1 ethyl acetate/ dichloromethane as the eluent to afford 872 mg (91%) of [11] methyl ester as a white solid: mp 81–82.5° C.; IR (neat) 3230, 2920, 2850, 1740, 1650 $cm^{-1}$; $^1H$ NMR (300 MHz, $CDCl_3/CD_3OD$) δ7.69 (dd, J=8.0, 1.5 Hz, 1H), 7.41(dt, J=8.0, 1.5 Hz, 1H), 6.96 (d, J=8.1 Hz, 1H), 6.91 (t, J=7.4 Hz, 1H), 5.02 (t, J=9.0 Hz, 1H), 4.65–4.60 (m, 2H), 4.43 (dd, J=8.8, 4.9 Hz, 1H), 3.73 (s, 3H), 3.62–3.55 (m, 2H), 2.43 (t, J=7.6 Hz, 2H), 1.95–1.26 (m, 32H), 0.91 (t, J=6.6 Hz, 3H); $^{13}C$ NMR (125 MHz, $CDCl_3$) δ176.18, 173.87, 172.95, 168.55, 161.02, 135.02, 129.50, 119.97, 117.70, 111.45, 70.43, 69.20, 53.85, 52.80, 33.26, 33.06, 31.82, 30.75, 30.62, 30.49, 30.46, 27.10, 25.95, 23.80, 23.72, 14.45; HRFABMS calcd. for $C_{33}H_{53}N_3O_7$ 604.3961, found 604.3975.

EXAMPLE 4

Cobactin [17]

To a mixture of 50 mg of unprotected cyclolysine [6] r=4 (0.35 mmol), 83 mg of Cbz protected serine (0.35 mmol) and 47.3 mg of HOAt (0.35 mmol) in 6 mL of freshly distilled DMF, 73.2 mg of EDC.HCl (0.38 mmol) was added. The reaction mixture was allowed to stand at room temperature for 2 h. The reaction mixture was then diluted with 20 mL of EtOAc. The organic layer was washed with 5% aqueous ascorbic acid (2×5 mL), saturated aqueous $NaHCO_3$ (1×5 mL), brine (2×5 mL), dried over $Na_2SO_4$, filtered and concentrated. The residue was purified silica chromatography with 10% of methanol in dichloromethane as the eluent to afford 121 mg (95%) of [17] as a white solid: $R_f$=0.40 (10% methanol in dichloromethane); mp 140–142° C.; IR (neat) 3306, 2930, 2846, 1710, 1644, 1060 $cm^{-1}$; $^1H$ NMR (300 MHz, $CDCl_3/CD_3OD$) δ7.46 (s, 5H), 6.41 (bd, 1H), 5.24 (s, 2H), 4.59 (m, 1H), 4.51–3.27 (m, 7H), 2.19–1.41 (m, 6H); $^{13}C$ NMR (75 MHz, $CDCl_3/CD_3OD$) δ170.30, 168.39, 156.29, 128.92, 128.35, 128.00, 127.82, 66.94, 62.74, 55.77, 52.00, 51.59, 30.01, 27.45, 25.55; HRFABMS calcd. for $C_{17}H_{24}N_3O_6$ 366.1665, found 366.1689.

EXAMPLE 5

N-Cbz Protected Mycobactin Analog [37 Y=H]

To a solution of 6.7 mg of Cbz protected serine (0.028 mmol), 4.0 mg of cyclolysine [6 r=4] (0.028 mmol) with 1 equiv of HOAt (4.0 mg) in 1 mL of freshly distilled DMF, 5.4 mg of EDC.HCl (0.028 mmol) was added. The resulting solution was allowed to stand at room temperature for 2.5 h. Upon disappearance of starting material based on TLC analysis, 16.5 mg of mycobactic acid [11] (0.028 mmol) with 0.056 mmol of EDC.HCl were introduced. Additional EDC HCl was added to accelerate the reaction. After standing at room temperature for 12 h, the reaction mixture was diluted with 10 mL of EtOAc. The organic portion was washed with water (2×5 mL), 0.5N HCl (1×5 mL), brine (2×5 mL), dried over $Na_2SO_4$, filtered and concentrated. The residue was purified by reverse phase $C_{18}$ silica gel chromatography with 1:1 methanol/acetonitrile as the eluent to afford 21.2 mg (81%) of [37 Y=H] as a white solid: $R_f$=0.40 on reverse phase $C_{18}$ silica gel TLC (methanol/acetonitrile= 1/1); mp 73.5–74.5° C.; IR (neat) 3300, 2905, 2856, 1775, 1660, 1635 $cm^{-1}$; $^1H$ NMR (300 MHz, $CDCl_3/CD_3OD$) δ7.64 (d, 1H, J=6.6 Hz), 7.37 (d, 1H, J=7.2 Hz), 7.28–7.25 (m, 5H), 7.07 (bd, 1H), 6.98 (m, 1H), 6.89–6.84 (m, 1H), 6.03 (bs, 1H), 5.06 (s, 1H), 4.92–4.89 (m, 2H), 4.65–4.48 (m, 4H), 4.33–4.25 (m, 2H), 4.85 (bs, 1H), 3.72–3.53 (m, 3H), 3.18 (bd, 1H), 2.60–2.49 (m, 1H), 2.40–2.38 (m, 1H), 1.97–1.41 (m, 40H), 0.83 (t, 3H, J=7.2 Hz); $^{13}C$ NMR (75 MHz, $CDCl_3/CD_3OD$) δ179.12, 176.73, 176.47, 170.47, 168.27, 167.71, 159.36, 156.18, 136.01, 134.25, 128.58, 128.47, 128.38, 128.03, 127.86, 119.12, 116.75, 109.86, 77.19, 69.36, 69.20, 69.06, 67.65, 66.99, 62.70, 55.60, 53.17, 50.21, 49.87, 49.59, 49.31, 49.11, 49.02, 48.73, 47.14, 33.91, 33.07, 31.79, 29.57, 29.36, 29.31, 29.23, 29.00, 24.65, 23.62, 23.44, 22.55, 13.96; HRFABMS calcd. for $C_{49}H_{73}N_6O_{12}$ 937.5286, found 937.5309.

EXAMPLE 6
N-Cbz Protected Mycobactin Analog [37] Y=Me

To a solution of 17.5 mg of Cbz protected threonine (0.069 mmol), 10 mg of cyclolysine (0.069 mmol) [6 r=4] with 1 equiv of HOAt (9.4 mg) in 6 mL of freshly distilled DMF, 13.3 mg of EDC.HCl (0.069 mmol) was added. The resulting solution was allowed to stand at room temperature for 2.5 h. Upon disappearance of starting material based on TLC analysis, 40 mg of mycobactic acid [11] (0.069 mmol) with 33.3 mg of EDC.HCl (0.173 mmol) was introduced. Additional EDC.HCl was added to accelerate the reaction. After standing at room temperature for 12 h, the reaction mixture was diluted with 25 mL of EtOAc. The organic portion was washed with water (2×5 mL), 0.5N HCl (1×5 mL), 5% ascorbic acid (2×5 mL), brine (2×5 mL), dried over $Na_2SO_4$, filtered and concentrated. The residue was purified by reverse phase $C_{18}$ silica gel chromatography with 1:3 methanol/acetonitrile as the eluent to afford 49 mg (75%) of [37 Y=Me] as a white solid: $R_f$=0.50 (10% methanol in EtOAc); mp 77.0–79.0° C.; IR (neat) 3300, 2925, 2835, 1780,1655 cm$^{-1}$; $^1$H NMR (600 MHz, CDCl$_3$) δ8.58 (bs, 1H), 7.66–7.62 (m, 2H), 7.41–7.35 (m, 1H), 7.30 (s, 5H), 7.00–6.93 (m, 1H), 6.89–6.84 (m, 1H), 6.08 (bs, 1H), 6.03 (bs, 1H), 5.07 (s, 2H), 4.95–4.91 (m, 1H), 4.67–4.52 (m, 4H), 4.31–4.25 (m, 2H), 3.91–3.89 (m, 1H), 3.63–3.52 (m, 3H), 2.44–2.40 (m, 2H), 2.18 (bs, 1H), 1.95–1.23 (m, 39H), 1.12 (bs, 3H), 0.86 (t, 3H, J=6.6 Hz); $^{13}$C NMR (150 MHz, CDCl$_3$) δ170.98, 170.32, 169.82, 169.21, 168.34, 167.53, 159.48, 156.52, 136.03, 134.18, 128.41, 128.32, 127.94, 127.77, 119.01, 116.77, 116.71, 109.79, 69.10, 67.60, 67.36, 66.94, 58.83, 53.09, 52.07, 50.82, 50.11, 49.05, 47.08, 33.01, 32.36, 31.76, 30.78, 29.56, 29.34, 29.29, 29.20, 28.96, 27.60, 25.57, 25.19, 24.58, 23.58, 23.38, 22.53, 21.79, 18.09, 13.98; HRFABMS calcd. for $C_{50}H_{75}N_6O_{12}$ 951.5443, found 951.5453.

EXAMPLE 7
Protected Cobactin [38]

To a mixture of 93 mg of N-Cbz β-alanine (0.42 mmol), 160 mg of amine [27] (0.42 mmol) and 1 equiv of HOAt (57 mg) in 3 mL of DMF, 1.1 equiv of EDC.HCl (88.3 mg) was added. After standing at room temperature for 2 h, the mixture was diluted with 20 mL of EtOAc and 5 mL of saturated aqueous NaHCO$_3$. The organic layer was then washed with water (2×5 mL), brine (2×5 mL), dried over Na$_2$SO$_4$, filtered and concentrated. The residue was purified by silica chromatography with 1.5:1 ethyl acetate/hexanes as the eluent to afford 224 mg (91%) of [38] as a colorless oil: $R_f$=0.40 (3:1 EtOAc/hexanes); IR (neat) 3320, 3080, 2950, 2865, 1720, 1660 cm$^{-1}$; $^1$H NMR (300 MHz, CDCl$_3$) δ7.75–7.70 (m, 5H), 7.45–7.34 (m, 10H), 6.72 (d, 1H, J=6.0 Hz), 5.46 (bs, 1H), 5.08 (s, 2H), 4.18 (dd, 1H, J=10.5, 6.0 Hz), 3.55–3.42 (m, 4H), 2.36 (t, 2H, J=5.7 Hz), 1.95–1.12 (m, 6H), 1.14 (s, 9H); $^{13}$C NMR (75 MHz, CDCl$_3$) δ170.32, 169.31, 156.29, 136.61, 136.13, 135.99, 132.01, 131.55, 130.27, 130.23, 128.44, 127.98, 127.56, 127.49, 77.2, 66.55, 54.21, 51.62, 33.92, 31.03, 27.30, 26.87, 25.31, 19.54; HRFABMS calcd. for $C_{33}H_{41}N_3O_5Si$ 588.2894, found 588.2874.

EXAMPLE 8
Mycobactin Analog [40a]

A slurry of 50 mg of cobactin [38] (0.082 mmol) with 15 mg of 10% Pd—C in 8 mL of MeOH was purged with a stream of N$_2$ over 10 min and subsequently with H$_2$ for an additional 15 min. The reaction mixture was stirred under H$_2$ (1 atm) at room temperature for 3 h. Then palladium catalyst was filtered off through a pad of Celite. The filtrate was concentrated to yield the corresponding free amine [39]. Without further purification, amine [39] was dissolved in a 2 mL of a DMF solution containing 42 mg of mycobactic acid [11] (0.073 mmol) and 10 mg of HOAt (0.073 mmol). To the above solution, 14 mg of EDC.HCl (0.073 mmol) was added. The resulting mixture was allowed to stand at room temperature for 3.5 h. The reaction was quenched by addition of 15 mL of EtOAc and 5 mL of H$_2$O. The organic mixture was then washed with water (2×5 mL), brine (2×5 mL), dried over Na$_2$SO$_4$, filtered and concentrated to give 60 mg of desired coupling product [40]. To a solution of 60 mg of [40] (0.06 mmol) with 6.9 mL of HOAc (0.12 mmol) in 2 mL of dry THF, 0.12 mL of 1M TBAF (0.12 mmol) in THF was added dropwise at 0° C. Then the reaction mixture was allowed to warm up to room temperature and stand for 1 h. After removal of solvents, the residue was purified by reverse phase $C_{18}$ silica gel chromatography with 3:2 methanol/acetonitrile as the eluent to afford 48.6 mg (85%) of [40a] as a white solid: $R_f$=0.55 on reverse phase $C_{18}$ silica gel TLC (3:1 methanol/acetonitrile); mp 173.5–175.0° C.; IR (neat) 3300, 2935, 2850, 1680, 1500 cm$^{-1}$; $^1$H NMR (300 MHz, CDCl$_3$/CD$_3$OD) δ7.65 (dd, 1H, J=7.8, 1.0 Hz), 7.41–7.35 (m, 1H), 6.99–6.96 (m, 1H), 6.88 (t, 1H, J=7.8 Hz), 5.00–4.95 (m, 1H), 4.66–4.49 (m, 3H), 4.33–4.30 (m, 1H), 3.89–3.51 (m, 5H), 3.22–3.15 (m, 1H), 2.48–0.95 (m, 42H), 0.85 (t, 3H, J=6.5 Hz); $^{13}$C NMR (125 MHz, CDCl$_3$/CD$_3$OD) δ175.16, 172.12, 170.76, 168.52, 167.33, 159.21, 155.32, 134.11, 128.51, 119.16, 116.72, 110.34, 77.20, 68.95, 67.79, 58.68, 53.58, 51.78, 51.51, 47.24, 36.40, 36.14, 32.34, 31.86, 31.21, 29.63, 29.59, 29.51, 29.46, 29.30, 29.11, 27.73, 25.74, 24.63, 23.84, 22.62, 21.82, 19.63, 14.05, 13.54; HRFABMS calcd. for $C_{41}H_{67}N_6O_9$ 787.4969, found 787.4969.

EXAMPLE 9
Protected Diaminopropionic Acid [16]

To the solution of 1.02 g of β-lactam [15] (3.49 mmol) in 18 mL 50% H$_2$O in THF, 125 mg of LiOH (5.22 mmol) was added. The resulting mixture was allowed to stand at room temperature for 3 h. Then the solution was acidified by addition of 8 mL of 2N HCl. The solution was then extracted with EtOAc (3×10 mL). The combined organic mixture was washed with H$_2$O (2×10 mL), brine (2×15 mL), dried over Na$_2$SO$_4$, filtered, and then concentrated to afford 1.08 g of acid [16] (100%) as a white solid: mp 132.0–134.0° C.; IR (neat) 3400, 3250, 2960, 2860, 1770, 1690 cm$^{-1}$; $^1$H NMR (300 MHz, CDCl$_3$/CD$_3$OD) δ7.29–7.17 (m, 5H), 4.58 (s, 2H), 4.08 (bt, 1H, J=5.1 Hz), 3.11 (d, 2H, J=5.1 Hz), 1.32 (s, 9H); $^{13}$C NMR (125 MHz, CDCl$_3$/CD$_3$OD) δ176.80, 156.15, 137.20, 128.13, 128.09, 127.60, 79.45, 75.41, 53.53, 53.00, 28.03; HRFABMS calcd. for $C_{15}H_{23}N_2O_5$ 311.1607, found 311.1617.

EXAMPLE 10
Protected Cobactin [9 R$_6$=Benzyloxy]

To a solution of 23 mg of amine [27] (0.061 mmol), 17 mg of Boc protected diaminopropionic acid (0.055 mmol) [16], 1.0 equiv of HOAt (7.5 mg, 0.055 mmol) and 7.4 mg of DMAP (0.055 mmol) in 0.5 mL of dry DMF, a pre-mixed solution of 0.055 mmol of EDC and 0.055 mmol of DMAP in 0.5 mL of dry DMF was added dropwise. The resulting mixture was allowed to stand at the room temperature for 6 h. The reaction mixture was then diluted with 15 mL of EtOAc and washed with water (2×5 mL), brine (2×5 mL), dried over Na$_2$SO$_4$, filtered and concentrated. The residue was purified by silica chromatography with 1:1 ethyl acetate/hexanes as the eluent to afford 33.8 mg (91%) of [9 R$_6$=benzyloxy] as a colorless oil: IR (neat) 3350, 2990, 2895, 1720, 1695 cm$^{-1}$; $^1$H NMR (300 MHz, CDCl$_3$) δ7.75–7.70 (m, 4H), 7.54 (bd, 1H), 7.42–7.27 (m, 11H), 5.95 (s, 1H), 5.48 (bd, 1H), 4.68 (s, 2H), 4.31 (bs, 1H), 4.24–4.16 (m, 1H), 3.51–3.40 (m, 1H), 3.35 (bs, 1H), 3.30 (d, 1H, J=5.1 Hz), 3.51 (dd, 1H, J=13.8, 6.3 Hz), 1.82–1.18 (m, 6H), 1.44 (s, 9H), 1.14 (s, 9H); $^{13}$C NMR (125 MHz, CDCl$_3$) δ169.86, 169.53, 155.71, 137.42, 136.14, 136.06, 132.10, 130.22, 130.18, 129.61, 129.46, 128.54, 128.39, 127.89, 127.56, 127.48, 76.63, 76.50, 76.04, 54.15, 53.36, 51.81, 30.85, 28.29, 27.29, 26.90, 25.36, 19.58; HRFABMS calcd. for C$_{37}$H$_{51}$N$_4$O$_6$Si 675.3578, found 675.3551.

EXAMPLE 11
N-Boc Protected Mycobactin Analog [8]

A slurry of 56 mg of cobactin [9 R$_6$=benzyloxy] (0.083 mmol) with 15 mg of 10% Pd—C was purged with a N$_2$ stream for 10 min and subsequently with H$_2$ for an additional 15 min. The reaction mixture was stirred under H$_2$ (1 atm) at 56° C. for 2 h. Then palladium catalyst was filtered off through a pad of Celite. The solution was concentrated to yield 45 mg of the corresponding free amine [10]. Without further purification, amine [10] was dissolved in 2 mL of a DMF solution containing 49 mg of mycobactic acid [11] (0.084 mmol) and 11.4 mg of HOAt (0.084 mmol). To the above solution, 16 mg of EDC.HCl (0.083 mmol) was added. The resulting mixture was allowed to stand at room temperature for 3 h. The reaction was quenched by addition of 20 mL of EtOAc and 5 mL of H$_2$O. The organic mixture then washed with water (2×5 mL), brine (2×5 mL), dried over Na$_2$SO$_4$, filtered and concentrated to give 84 mg of desired coupled product [12] in 89% yield. To a solution of 37 mg of [12] (0.032 mmol) with 5.6 uL of HOAc (0.097 mmol) in 2 mL of dry THF, 0.1 mL of 1M TBAF (0.1 mmol) in THF was added dropwise at 0° C. Then the reaction mixture was allowed to warm up to room temperature and stand for 1 h. After removal of solvents, the residue was purified by reverse phase C$_{18}$ silica gel chromatography with 1:8 methanol/acetonitrile as the eluent to afford 27.6 mg {85% from [9 R$_6$=benzyloxy]} of [8] as a white solid: R$_f$=0.30 on reverse phase C$_{18}$ silica gel TLC(1:8 methanol/acetonitrile); mp 164.5–165.5° C.; IR (neat) 3390, 3090, 2990, 2850, 1690, 1670 cm$^{-1}$; $^1$H NMR (500 MHz, CDCl$_3$/CD$_3$OD) δ7.62 (d, 1H, J=7.5 Hz), 7.35 (t, 1H, J=8.0 Hz), 6.94 (d, 1H, J=8.0 Hz), 6.84 (t, 1H, J=7.5 Hz), 4.94 (t, 1H, J=9.0 Hz), 4.91–4.58 (m, 1H), 4.55–4.51 (m, 1H), 4.50–4.47 (m, 1H), 4.12 (bs, 2H), 3.85–3.81 (m, 1H), 3.78–3.76 (m, 1H), 3.69–3.66 (m, 1H), 3.57–3.51 (m, 3H), 3.37 (t, 2H, J=7.5 Hz), 1.91–1.83 (m, 40H), 1.38 (s, 9H), 0.82 (t, 3H, J=6.5 Hz); $^{13}$C NMR (125 MHz, CDCl$_3$/CD$_3$OD) δ175.15, 172.60, 171.02, 170.68, 168.81, 167.17, 159.20, 155.21, 133.95, 128.39, 119.02, 116.60, 109.99, 80.00, 77.20, 68.97, 67.65, 54.15, 53.35, 51.96, 51.88, 47.21, 41.06, 32.25, 31.78, 30.62, 29.56, 29.52, 29.44, 29.39, 29.33, 29.22, 28.78, 28.12, 27.59, 25.68, 24.61, 22.55, 22.06, 13.95; HRFABMS calcd. for C$_{46}$H$_{76}$N$_7$O$_{11}$ 902.5603, found 902.5595.

We claim:
1. The compound of the formula

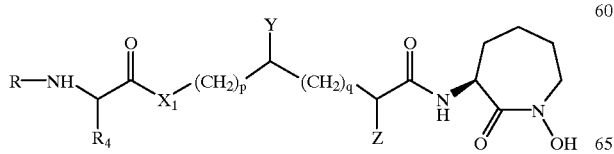

wherein R is a 2-phenyloxazoline of the formula (1a)

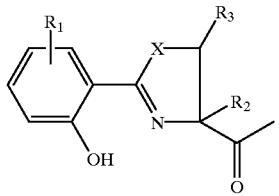

(1a)

or a 2-phenyloxazole of the formula (1b)

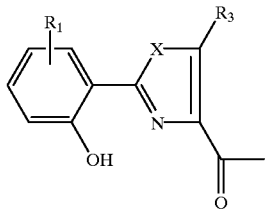

(1b)

wherein R$_1$ is hydrogen, lower alkyl, lower alkoxy, hydroxy, carboxy, amino, mono- or dialkylamino, aminocarbonyl, mono- or dialkylaminocarbonyl, or C$_1$–C$_4$ alkyl substituted by one or two phenyl groups;

R$_2$ and R$_3$ independently are hydrogen or C$_1$–C$_3$ alkyl;

p and q independently are 0, 1 or 3;

R$_4$ is a siderophoric group of the formula

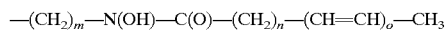

wherein m is an integer of from 2 to 6, n is 0 or an integer of from 1 to 22, and o is 0 or an integer 1 to 4, provided that m+o is no greater than 25;

X$_1$ is O or NH;

Y is H or C$_1$–C$_4$ alkyl;

Z is H, lower alkyl, mono- or dialkylamino, or —N(R$_5$)(R$_5$') when X$_1$ is NH; and when X$_1$ is O, Z is mono- or dialkylamino or —NR$_5$)(R$_5$');
wherein R$_5$ is hydrogen, lower alkyl, alkyloxycarbonyl, aryloxycarbonyl, aralkyloxycarbonyl, cycloalkoxycarbonyl, bicycloalkyloxycarbonyl, or lower alkanoyl;

R$_5$' is hydrogen or lower alkyl;

or the pharmaceutically acceptable salts thereof.

2. The compound of claim 1 wherein X$_1$ is NH and Z is —N(R)(R$_5$').

3. The compound of claim 2 wherein R$_5$ is alkyloxycarbonyl and R$_5$' is hydrogen.

4. The compound of claim 3 wherein R$_5$ is t-butyloxycarbonyl, q=0, Y=H. and p=0.

5. The compound of claim 4 of the formula 8

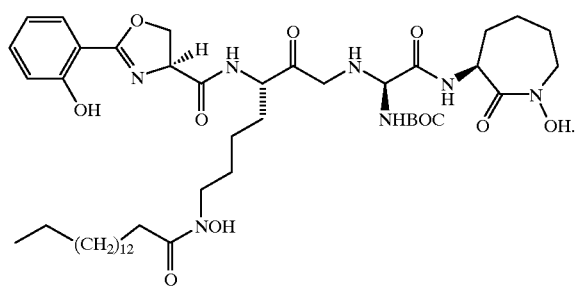
[8]

6. The compound of claim 1 wherein $X_1$ is NH and Z and Y are hydrogen.

7. The compound of claim 6 wherein q=1, p=0, R is the group of the formula

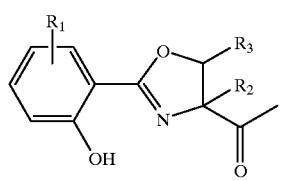

wherein $R_1$, $R_2$ and $R_3$ are hydrogen and $R_4$ is the group of the formula

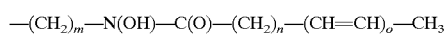

wherein m=4, n=15 and o=0.

8. The compound of claim 1 wherein $X_1$ is O.

9. The compound of claim 8 wherein Z is —N($R_5$)($R_5$') and $R_5$' is hydrogen.

10. The compound of claim 9 wherein $R_5$ is —NHBOC and Y is hydrogen.

11. The compound of claim 10 of the formula 37

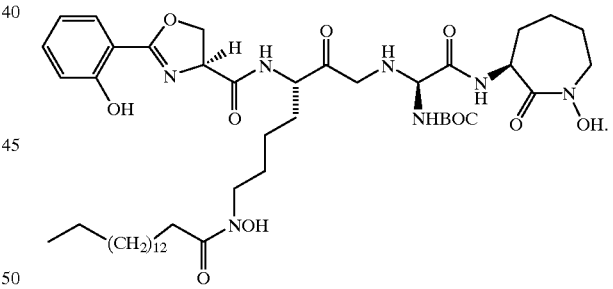
[37]

12. The compound of claim 9 wherein Y is methyl and Z is —NHBOC.

13. The method for treating *Mycobacterium tuberculosis* infections in man which comprises administering to said man an effective non-toxic amount of a compound of claim 1 or a pharmaceutically acceptable non-toxic salt thereof.

14. The method of claim 13 wherein the compound of the formula 8

[8]

is administered.

15. A pharmaceutical formulation comprising a compound of claim 1 or a non-toxic pharmaceutically acceptable salt thereof and a pharmaceutically acceptable carrier.

16. The formulation of claim 15 comprising compound 6 of the formula

[8]

* * * * *